United States Patent
Wang

(10) Patent No.: US 11,285,166 B2
(45) Date of Patent: Mar. 29, 2022

(54) GLYCAN-BASED DRUGS, THERAPIES AND BIOMARKERS

(71) Applicant: B&H Biotechnologies, Willowbrook, IL (US)

(72) Inventor: Huiru Wang, Willowbrook, IL (US)

(73) Assignee: B&H BIOTECHNOLOGIES, LLC, Willowbrook, IL (US)

( * ) Notice: Subject to any disclaimer, the term of this patent is extended or adjusted under 35 U.S.C. 154(b) by 0 days.

(21) Appl. No.: 16/435,098

(22) Filed: Jun. 7, 2019

(65) Prior Publication Data

US 2019/0388447 A1 Dec. 26, 2019

Related U.S. Application Data

(60) Division of application No. 14/803,725, filed on Jul. 20, 2015, now Pat. No. 10,342,812, which is a division of application No. 12/900,913, filed on Oct. 8, 2010, now Pat. No. 9,119,866, which is a continuation-in-part of application No. PCT/US2009/039810, filed on Apr. 7, 2009.

(60) Provisional application No. 61/335,415, filed on Jan. 7, 2010, provisional application No. 61/278,685, filed on Oct. 9, 2009, provisional application No. 61/043,396, filed on Apr. 8, 2008.

(51) Int. Cl.

| | |
|---|---|
| *A61K 31/7012* | (2006.01) |
| *A61K 31/198* | (2006.01) |
| *A61K 31/7008* | (2006.01) |
| *A61K 36/8962* | (2006.01) |
| *A61K 39/00* | (2006.01) |
| *C40B 60/12* | (2006.01) |
| *A61K 31/70* | (2006.01) |

(52) U.S. Cl.
CPC ........ *A61K 31/7012* (2013.01); *A61K 31/198* (2013.01); *A61K 31/70* (2013.01); *A61K 31/7008* (2013.01); *A61K 36/8962* (2013.01); *A61K 39/00* (2013.01); *C40B 60/12* (2013.01); *A61K 2039/6056* (2013.01); *B01J 2219/00659* (2013.01); *B01J 2219/00731* (2013.01); *G01N 2400/02* (2013.01); *G01N 2400/12* (2013.01); *G01N 2400/38* (2013.01); *G01N 2500/00* (2013.01)

(58) Field of Classification Search
CPC .... A61K 31/7008; A61K 39/00; A61K 31/70; A61K 31/198; A61K 31/7012; A61K 36/8962; A61K 2039/6056; C40B 60/12; A61P 37/04; B01J 2219/00731; B01J 2219/00659; G01N 2400/38; G01N 2400/12; G01N 2500/00; G01N 2400/02
See application file for complete search history.

(56) References Cited

U.S. PATENT DOCUMENTS

| | | |
|---|---|---|
| 3,720,760 A | 3/1973 | Bennich et al. |
| 4,039,681 A | 8/1977 | Abdel-Monem |
| 4,447,600 A | 5/1984 | Ogura et al. |
| 4,537,769 A | 8/1985 | Cerini |
| 4,762,822 A | 8/1988 | Ettinger |
| 4,918,177 A | 4/1990 | Yoshimura et al. |
| 5,077,397 A | 12/1991 | Yoshimura et al. |
| 5,393,742 A | 2/1995 | Ishii et al. |
| 5,438,125 A | 8/1995 | Okamoto et al. |
| 5,639,734 A | 6/1997 | Esko et al. |
| 5,719,020 A | 2/1998 | Liav et al. |
| 6,288,041 B1 | 9/2001 | Chaki et al. |
| 6,444,649 B1 | 9/2002 | Inamori et al. |
| 6,524,593 B1 | 2/2003 | Yu et al. |
| 6,664,235 B1 | 12/2003 | Kanie et al. |
| 7,666,446 B2 | 2/2010 | Choi et al. |
| 8,241,886 B2 | 8/2012 | Truong-Le et al. |
| 8,268,354 B2 | 9/2012 | Truong-Le et al. |
| 8,337,826 B2 | 12/2012 | Tschope et al. |
| 2004/0259142 A1 | 12/2004 | Chai et al. |
| 2007/0048354 A1 | 3/2007 | Wassenaar |
| 2008/0003330 A1 | 1/2008 | Rueda et al. |
| 2010/0008938 A1 | 1/2010 | Diwan et al. |
| 2011/0243988 A1 | 10/2011 | Ohtake et al. |

FOREIGN PATENT DOCUMENTS

| | | | | |
|---|---|---|---|---|
| EP | 0775152 B1 | 5/1999 | | |
| JP | H08337532 A | 12/1996 | | |
| WO | WO-03041639 A2 * | 5/2003 | ......... | A61K 31/7024 |
| WO | WO2008021493 A3 | 2/2008 | | |

(Continued)

OTHER PUBLICATIONS

Brosnan et al. The sulfur-containing amino acids: an overview. J. Nutr. 2006. vol. 136. No. 6, pp. 1636S-1640S.
Karkas et al., "Studies of the stability of simple derivatives of sialic acid," J. Biol. Chem. 1964, vol. 239, pp. 949-957.
Shaw et al. "Detection of CMP-N-acetylneuraminic acid hydroxylase activity in fractionated mouse liver," Biochem. J. 1989, vol. 263, pp. 355-363.

(Continued)

*Primary Examiner* — Shafiqul Haq
(74) *Attorney, Agent, or Firm* — McDonnell Boehnen Hulbert & Berghoff LLP

(57) ABSTRACT

The present disclosure discloses simple and efficient glycan- or carbohydrate-based processes or methods for the rapid identification of biological markers and therapeutic targets especially glycan-related targets of infectious diseases, cancers, autoimmune diseases, allergies, inflammation, toxicity, obesity and/or other disorders of humans, animals, plants and other organisms. Therefore, novel methods and products for the diagnosis, prevention, and treatment of such diseases obtainable based on these therapeutic targets can be developed.

11 Claims, 9 Drawing Sheets

(56) References Cited

FOREIGN PATENT DOCUMENTS

WO     WO2012054067 A1     4/2012

OTHER PUBLICATIONS

Wang et al. The role and potential of sialic acid in human nutrition. European Journal of Clinical Nutrition 2003, vol. 57, pp. 1351-1369.

* cited by examiner

Binding of WGA and SBA to tissue sections of healthy adult mice

Binding of an anti-RV antibody and WGA to tissue sections of bulb/c mice

FIG. 11

GLYCAN-BASED DRUGS, THERAPIES AND BIOMARKERS

CROSS-REFERENCE TO RELATED APPLICATIONS

This application is a divisional of U.S. application Ser. No. 14/803,725, filed Jul. 20, 2015, which is a divisional of U.S. application Ser. No. 12/900,913, filed Oct. 8, 2010, now U.S. Pat. No. 9,119,866, issued Sep. 1, 2015, which claims the benefit of priority from U.S. Provisional Application No. 61/278,685, filed Oct. 9, 2009, and U.S. Provisional Application No. 61/335,415, filed Jan. 7, 2010, and which is a continuation-in-part of PCT Application No. PCT/US2009/39810, filed on Apr. 7, 2009, which claims the benefit of priority from U.S. Provisional Application No. 61/043,396, filed Apr. 8, 2008. The disclosures of each of these applications are explicitly incorporated by reference herein in their entirety.

FIELD OF INVENTION

The present disclosure relates generally to the fields of biology, medicine and epidemiology, and in particular, to one or more processes for diagnosing, preventing and/or treating infectious diseases, cancers, autoimmune diseases, allergies, toxicity, obesity and/or other disorders of humans, animals, plants and other organisms. More specifically, the present disclosure relates to processes for the identification of therapeutic targets of the disorders mentioned above and the uses thereof.

BACKGROUND

Carbohydrates are an essential component of life as a structural and energy storage component, and as stabilization, recognition, signaling and communication agents. Increasing interest in glycobiology has been precipitated by recent findings that cell surface carbohydrates are critically involved in cell adhesion and, thus, in cell-cell interaction. The advent of molecular biology in this field has enabled scientists to manipulate carbohydrate expression and study glycoprotein function.

Difficulties in the Study of Sugar Structures

Part of the variability seen in saccharide structures is due to the fact that monosaccharide units may be coupled to each other in many different ways, as opposed to the amino acids of proteins or the nucleotides in DNA, which are always coupled together in a standard fashion. The study of saccharide structures is also complicated by the lack of a direct template for their biosynthesis, contrary to the case with proteins where their amino acid sequence is determined by their corresponding gene.

Saccharides are also secondary gene products and as such are generated by the coordinated action of many enzymes in the subcellular compartments of a cell. Thus, the structure of a saccharide may depend on the expression, activity and accessibility of the different biosynthetic enzymes. This means it is not possible to use recombinant DNA technology in order to produce large quantities of saccharides for structural and functional studies as has been used extensively for protein studies.

SUMMARY OF THE INVENTION

Aspects of the present disclosure are based on the concepts that cell surface glycans or carbohydrates are critically involved in cell-cell interaction; that in at least some form, glycans or carbohydrates are shared by some or all organisms during life origination and evolution; and that carbohydrates changes at different physical status. Thereof, the present disclosure illustrates simple and efficient glycan- or carbohydrate-based processes or methods for the rapid identification of biological markers and therapeutic targets especially glycan-related targets that are related to infectious diseases, cancers, autoimmune diseases, allergies, inflammation, toxicity, obesity and/or other disorders of humans, animals, plants and other organisms. The process according to the present disclosure in one embodiment is characterized by the following operations:

1) the attachment and/or fixation of healthy and disease cells and/or tissues of organisms, pathogens, glycans, lectins, glycan recognition systems, antibodies and/or sera, herbs, small molecules and toxins (all called target candidates hereafter) to at least one solid carrier for an array or microarray (called array carrier hereafter);

2) the binding of an antibody or a serum, a pathogen, a glycan, a lectin, a glycan recognition system, a herb, a small molecule or a toxin (all called "detection candidates" hereafter) to the array carrier/carriers;

3) the detection of the binding of a detection candidate to the target candidates on the array carrier/carriers;

4) the detection of the biological function, pathogenesis, pharmacology, toxicity of a detection candidate with positive binding to at least one of the targets attached on the array carrier/carriers, in animal experiments and/or cell or tissue culture systems;

5) the application of the detection candidates relevant to infectious diseases, autoimmune diseases, allergies, cancers, obesity and other disorders determined in step 4 for the diagnosis, prevention and treatment of these disorders; for drug discovery and delivery; for vaccine development and to the fields of epidemiology and biology especially developmental and evolutionary biology;

6) the identification of the therapeutic targets or markers of the healthy and/or disease tissues and cells of organisms (attached on the array carrier/carriers) bound by at least one detection candidate;

7) the application of the therapeutic targets or markers identified in step 6, their derivatives (including but not limited to analogs, agonists, antagonists, variants, mutants, fragments, synthetic peptides, recombinant antigens) and any other forms of the therapeutic targets for the diagnosis, prevention, treatment and drug delivery of infectious diseases, autoimmune diseases, allergies, cancers, obesity and other disorders related to at least one of the therapeutic targets with known or unknown etiology and/or pathogenesis.

Accordingly, in one embodiment the present disclosure is to provide simple and efficient processes or methods for the rapid identification of therapeutic targets; for the discovery of drugs and drug delivery systems; for the pathogenesis studies and cause screening of infectious diseases, autoimmune diseases, allergies, toxicity, cancers, inflammation, obesity and other disorders of humans, animals, plants and other organisms; for development of high quality and new vaccines; for effective control of pandemic diseases; for functional, toxic, pharmacological and pharmaceutical studies of lectins, herbs, toxins and small molecules; for development of animal models of autoimmune diseases, allergies, toxicity, cancers, obesity and other disorders; and for studies of epidemiology and biology especially evolutionary biol-

BRIEF DESCRIPTION OF THE DRAWINGS

Figure 11:
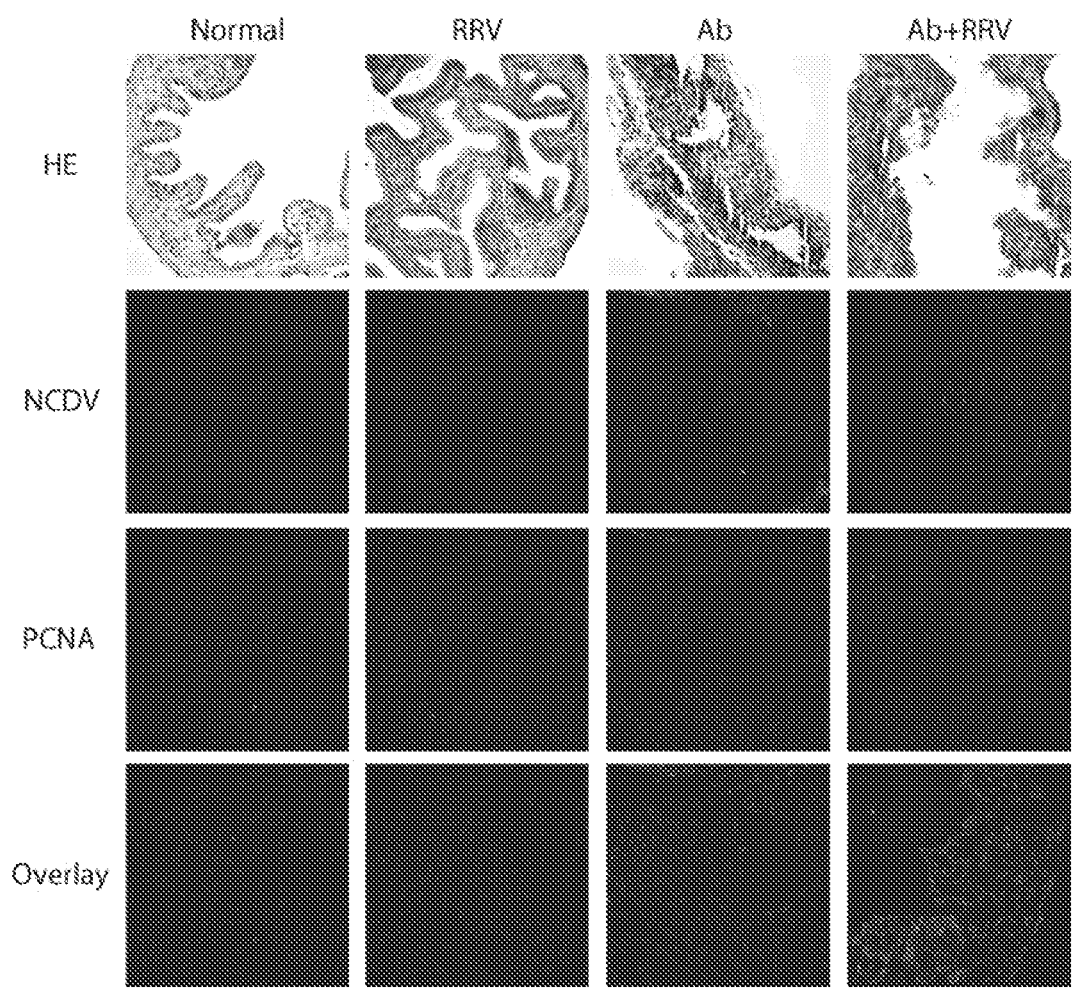

FIG. 11 is a graphical representation of detection of binding of anti-rotavirus antibodies (NCDV) and a proliferation marker (PCNA) to tissue sections of RRV infected and uninfected mouse pups.

DETAILED DESCRIPTION OF THE PREFERRED EMBODIMENT(S)

Figure 1:
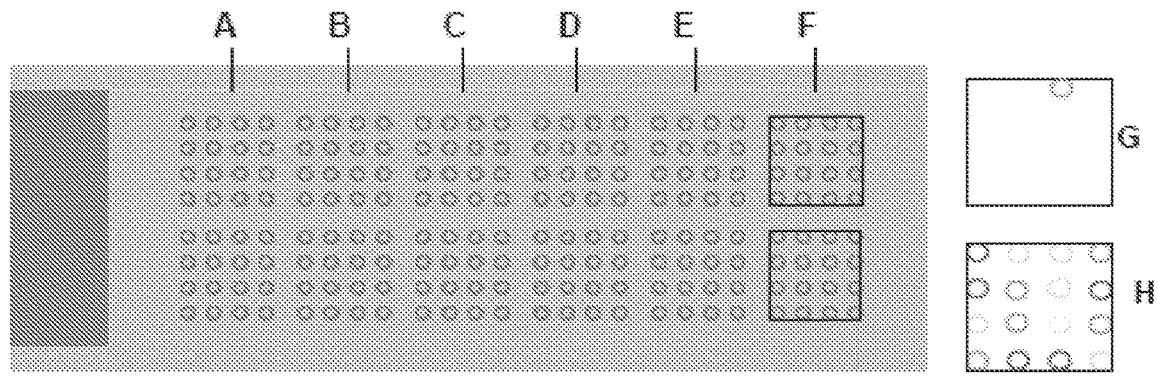
FIG. 1 is a graphical representation of an example array chip.

While the present disclosure is susceptible of embodiment in many different forms, there will be described herein in detail, preferred and alternate embodiments of the present disclosure. It should be understood however, that the present disclosure is to be considered an exemplification of the principles of the invention and is not intended to limit the spirit and scope of the invention and/or claims of the embodiments illustrated.

Array Carriers and Attachment or/and Fixation of Materials and Chemicals

In the present disclosure, a solid carrier (called array carrier hereafter) for the use of array or microarray refers to an object which can be used for attachment of materials of organisms and chemicals include but not limited to a slide, a plate, a membrane, a strip, a chip, or a particle, etc., without limitation. Materials of organisms and chemicals can be attached or fixed to at least one array carrier. The methods for attachment and fixation of materials of organisms and chemicals to a solid carrier can be physical, chemical, biological and all the other ways known in the arts.

Materials and Chemicals for Primary Screening

According to the disclosure, materials of organisms and chemicals include but are not limited to the following.

Organism and Pathogens

In the present disclosure, the term organism refers to an individual living system including but not limited to animals, plants, insects, fungi or micro-organisms. Based on cell type, organisms can be divided into the prokaryotic and eukaryotic groups. The prokaryotes are generally considered to represent two separate domains, called the Bacteria and Archaea. Eukaryotic organisms include but not limited to humans, animals, plants, fungi, slime mould, algae, organelles, mitochondria and (in plants) plastids, viral eukaryogenesis, etc. More recently a clade, Neomura, has been proposed, by Thomas Cavalier-Smith, which groups together the Archaea and Eukarya. Cavalier-Smith also proposed that the Neomura evolved from Bacteria, more precisely from Actinobacteria.

A microorganism (also can be spelled as micro organism) or microbe is an organism that is microscopic (too small to be seen by the naked human eye). One aspect of the present disclosure relates to microorganisms including but not limited to beneficial microorganisms, archaea, pathogenic microorganisms responsible for illness and/or organisms related to life evolution. More specifically, microorganisms include but not limited to bacteria, viruses, fungi, viroids, prions, etc.

As used herein, a "pathogen" refers to a pathogenic organism including but not limited to a microorganism, a parasite, an insect, a plant, and etc., without limitation. The term "infectious diseases" refers to the detrimental colonization of a host organism by a foreign species. Pathogens specific to infectious diseases suitable for use in this process include, but are not limited to, viruses, bacteria, parasites, fungi, viroids, prions, protozoa, and insects.

Types of pathogens include but are not limited to any types of pathogens, live or dead or inactivated, fresh or dried, fixed or frozen, whole or part or fragment, sections, smears, homogenates, lysates, and extracts of pathogens, and etc., without limitation.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, F.sub.ab, F.sub.ab' and F(ab').sub.2 fragments, and an Fab expression library. In general, an antibody molecule obtained from humans relates to any of the classes IgG, IgM, IgA, IgE and IgD, which differ from one another by the nature of the heavy chain present in the molecule. Certain classes have subclasses as well, such as IgG.sub.1, IgG.sub.2, and others. Furthermore, in humans, the light chain may be a kappa chain or a lambda chain. Reference herein to antibodies includes a reference to all such classes, subclasses, antibody fragments and types of human antibody species. Natural occurring antibodies are found in blood or other bodily fluids of vertebrates.

Antibodies suitable for use in this disclosure can be specific for any organisms, any pathogens, any infectious agents, any glycans, any glycoconjugates, any "self" antigens or any biological markers of an organism, and etc., without limitation. Sera from patients diagnosed infectious diseases, autoimmune diseases, allergies, toxicity, cancers, obesity and other disorders are also included.

Preferably antibodies to viruses suitable for use in this process include but not limited to any types of antibodies or antibody fragments to dsDNA viruses including but not limited to adenoviridea, herpesviridea, papovaviridea, poxviridea; the ssDNA viruses including but not limited to circoviridea, geminiviridae, parvovirinae; dsRNA viruses including but not limited to birnaviridae, reoviridea, (+)sense RNA viruses including but not limited to astroviridea, caliciviridea, coronaviridea, flaviviridea, picornaviridea, potyviridea, tabamoviridea, togaviridea; (–)sense RNA viruses including but not limited to filoviridea, paramyxoviridea, pneumovirinae, rhabdoviridea, arenavirus, bunyaviridea, orthomyxoviridea; RNA reverse transcribing viruses including but not limited to retroviridea; DNA reverse transcribing viruses including but not limited to badnavirus, caulimoviridea, hepadnaviridea; satellites including but not limited to tobacco necrosis virus satellite; hepatitis delta virus; viroids including but not limited to potato spindle tuber viroid, and agents of spongiform encephalopathies. More specifically, antibodies to viruses include but not limited to any types of antibodies to reovirus, rotavirus, cytomegalovirus, influenza virus including avian influenza A virus, Epstein-Barr virus, hepatitis virus, HIV, HTLV, papilloma virus, polio virus, parainfluenza virus, measles virus, mumps virus, respiratory syncytial virus, shipping fever virus, Western and Eastern encephalomyelitis virus, Japanese B encephalomyelitis virus, Russian spring-summer encephalomyelitis virus, hog cholera virus, pox virus, rabies, virus, distemper virus, foot and mouth disease virus, rhinovirus, Newcastle disease virus, vaccinia virus; and pseudorabies virus, etc without limitation.

Preferably antibodies to bacteria suitable for use in this process include but not limited to any types of antibodies or antibody fragments to Gram-positive and Gram-negative bacteria, or bacilli (rod-shaped), cocci (spherical) and spirilla (curved walls), and other bacteria. Specific bacteria include but not limited to cholera, syphilis, anthrax, leprosy and bubonic plague, rickettsias, *Neisseria gonorrhoeae, Bordetella pertussis, Escherichia coli, Salmonella enterica, Vibrio cholerae, Pseudomonas aeruginosa, Yersinia pestis, Francisella tularensis, Haemophilus influenzae,* purple sulfur bacteria, *Helicobacter pylori, Campylobacter jejuni, Bacillus anthracis/cereus/thuringiensis, Clostridium tetani, Clostridium botulinum,* staphylococci, streptococci, pneumococci, *Streptococcus pneumoniae,* mycoplasmas, *Bacteroides fragilis, Mycobacterium tuberculosis, Mycobacterium leprae, Corynebacterium diphtheriae, Treponema pallidum, Borrelia burgdorferi, Chlamydia trachomatis, Chlamydia psittaci,* phycocyanin, phycoerythrin, mitochondria, chloroplasts, etc., without limitation.

Cells, Tissues and Organs of Organisms

As used herein, the term of disease refers to an abnormal condition of an organism that impairs bodily functions, associated with specific symptoms and signs in human beings or animals, "disease" is often used more broadly to refer to any condition that causes discomfort, dysfunction, distress, social problems, and/or death to the person afflicted, or similar problems for those in contact with the person or the animal. In this broader sense, it sometimes includes disabilities, disorders, syndromes, infectious diseases, isolated symptoms, deviant behaviors, and atypical variations of structure and function, while in other contexts and for other purposes these may be considered distinguishable categories. Types of diseases include but not limited to infectious diseases, cancers, autoimmune diseases, allergies, toxicity, obesity and/or other disorders of humans, animals, plants and other organisms.

Types of healthy or normal and disease cells, tissues and/or organs of eukaryotes according to the present disclosure can be any types of cells being cultured in vitro including but not limited to various cell lines and primary cells known in the art; any types of cells being obtained from fresh tissues; any types of fragments, sections or smears of fresh, frozen or fixed tissues or organs; extracts or homogenates or lysates of cells or tissues or organs, any types of organ parts, or any other types of cells, tissues or organs, without limitation.

Healthy and disease cells or tissues or organs of humans, animals or plants include their either part or intact period of life time from embryo, fetal, newborn, young child to adult. The healthy and not healthy tissues or organs of humans and animals can be but not limited to epithelium and glands; connective tissue; muscle including smooth, skeletal and cardiac muscle; nervous tissue including central nervous system (CNS) and peripheral nervous system (PNS); cartilage, bone and joints; extracellular matrix; blood and hemopoiesis; bone marrow; cardiovascular system including heart, arteries, capillaries and veins; respiratory system including lungs, bronchial tree, alveolar duct and alveoli, digestive system including oral cavity, esophagus, stomach, small intestine (duodenum, jejunum, and ileum), and large intestine (cecum, colon, rectum, anal canal and appendix), salivary glands, pancreas, liver, bile duct and gallbladder; urinary system including kidneys, ureter, bladder, and urethra; female reproductive system including ovaries, oviducts, uterus and vagina; male reproductive system including testes, genital ducts, penis, seminal vesicles, prostate gland, and bulbourethral glands; lymphois (immune) system including lymph nodes, thymus and spleen; endocrine glands including pineal body, pituitary gland, thyroid gland, parathyroid glands and suprarenal glands; integument including skin and its appendages, sweat glands, sebaceous glands, hair and nails.

Glycans and Glycoconjugates

The term glycan refers to a polysaccharide, or oligosaccharide. An oligosaccharide is a saccharide polymer containing a small number (typically three to ten) of component sugars, also known as simple sugars. Glycans usually consist of O- or N-glycosidic linkages of monosaccharides to compatible amino acid side chains in proteins or to lipid moieties. Two types of glycosylation exist: N-linked glycosylation to the amide nitrogen of asparagine side chains and O-linked glycosylation to the hydroxy oxygen of serine and threonine side chains. Other glycans include but not limited to O-GlcNAc, GAG Chain, glycosaminoglycans, and glycosphinglipid. Monosaccharides include but not limited to fructose, glucose, mannose, fucose, xylose, galactose, lactose, N-acetylgalactosamine, N-acetylglucosamine, and sialic acids. O- and N-linked glycans are very common in eukaryotes but may also be found, although less commonly, in prokaryotes. Glycans can be found attached to proteins as in glycoproteins and proteoglycans. They are generally found on the exterior surface of cells. Sialic acid is a generic term for the N- or O-substituted derivatives of neuraminic acid, a nine-carbon monosaccharide. Some members of this group include N-acetylneuraminic acid (Neu5Ac or NANA), 2-Keto-3-deoxynononic acid (Kdn), N-Acetylglucosamine (GlcNAc), N-Acetylgalactosamine (GalNAc), N-Acetylmannosamine (ManNAc), and N-Glycolylneuraminic acid (Neu5Gc). Sialic acids are found widely distributed in animal tissues and in bacteria, especially in glycoproteins and gangliosides. The amino group bears either an acetyl or a glycolyl group. The hydroxyl substituents may vary considerably: acetyl, lactyl, methyl, sulfate and phosphate groups have been found. Sialic acid rich glycoproteins bind selectin (Ctype lectin) in humans and other organisms.

Glycanconjugates

In the present disclosure, the term glycan also refers to the carbohydrate portion of a glycoconjugate, include but not limited to glycoproteins, glycolipids, proteoglycans and glycophosphosphingolipids or any other known or unknown glycoconjugates. Glycoconjugates are found predominantly on the outer cell wall and in secreted fluids. Glycoconjugates have been shown to be important in cell-cell interactions due to the presence on the cell surface of various glycan binding receptors in addition to the glycoconjugates themselves. en.wikipedia.org/wiki/Glycobiology—_note-Ma_2004

The term of proteoglycans represent a special class of glycoproteins that are heavily glycosylated. They consist of a core protein with one or more covalently attached glycosaminoglycan (GAG) chain(s). These glycosaminoglycan chains are long, linear carbohydrate polymers that are negatively charged under physiological conditions, due to the occurrence of sulfate and uronic acid groups. Proteoglycans can be categorised depending upon the nature of their glycosaminoglycan chains. These chains include but not limited to chondroitin sulfate and dermatan sulfate; heparin and heparan sulfate; keratan sulfate. Proteoglycans can also be categorised by size. Examples of large proteoglycans are aggrecan, the major proteoglycan in cartilage, and versican, present in many adult tissues including but not limited to blood vessels and skin. The small leucine rich repeat proteoglycans (SLRPs) include but not limited to decorin, biglycan, fibromodulin and lumican.

The term of glycolipids refers to carbohydrate-attached lipids. They occur where a carbohydrate chain is associated with phospholipids on the exoplasmic surface of the cell membrane. They extend from the phospholipid bilayer into the aqueous environment outside the cell where it acts as a recognition site for specific chemicals as well as helping to maintain the stability of the membrane and attaching cells to one another to form tissues. Glycolipid includes but not limited to galactolipids, sulfolipids (SQDG), glycosphingolipids, cerebrosides, galactocerebrosides, glucocerebrosides, glucobicaranateoets, gangliosides, globosides, sulfatide, glycophosphosphingolipids, or any other known or unknown glycolipids.

Glycan Recognition System

Glycans, which are assumed to have been first synthesized in the form of simple homopolysaccharides (amylose, cellulose, etc.), are understood to have evolved into more complex hetero-polysaccharides. This evolution is assumed to have triggered the advent of proteins (lectins) related to the "recognition system of glycans" that recognizes each structure, identifies molecules, introduces biological signaling and facilitates infectious diseases. The synthesis system and the recognition system of glycans depend on each other and are still considered to be undergoing co-evolution.

Recognition system of glycans includes but not limited to lectins including animal-, plant-, and pathogen-lectins, enzyme containing carbohydrate recognition domain (CRD), antibodies against glycans, cytokines, chaperone and transport proteins, microbial carbohydrate-binding croteins, clycosaminoglycan-binding proteins, or any other known or unknown glycan recognition systems, without limitation.

Lectins are sugar-binding proteins which are highly specific for their sugar moieties. In the present disclosure, lectins include but not limited to animal lectins, plant lectins, pathogen lectins, and any other know or unknown lectins. Lectins occur ubiquitously in nature which typically contains an evolutionarily conserved carbohydrate-recognition domain. Lectins are known to play important roles in the immune system by recognizing carbohydrates that are found exclusively on pathogens, or that are inaccessible on host cells. Pathogenic lectins from virus, bacteria, protozoa and insects are involved in infection through their sialic acid-recognizing activity.

Animal lectins include but not limited to C-type, M-type, L-type, P-type, R-type, I-type, F-type, F-box H-type lectins, galectins, pentraxin, spider toxin, tachylectin, chitin-binding protein, chitinase-like lectins, TIM-lectin, calnexin-calreticulin, ficolins, fucolectin, intelectins, and any other types of know or unknown animal lectins.

Plant lectins include but not limited to β-prism I lectin, β-prism II lectin, β-trefoil lectin, knottin, legume lectin, fructose-, mannose-, glucose-, fucose-, galactose-, Nacetylgalactosamine-, and N-acetylglucosamine-specific lectins, and any other types of know or unknown plant lectins.

Pathogen lectins include but not limited to bacterial lectins, virus lectins and fungal lectins. Bacterial lectins include but not limited to AB 5 toxin, bacterial neurotoxin, staphylococcal toxin, pili adhensin, cyanobacterial lectins, 1-Ca β-sandwich, 2-Ca βsandwich, β-propeller, toxin repetitive domain. Virus lectins include but not limited to coat protein, hemmagglutinin, tailspike protein, capsid spike protein and fiber knob. Fungal lectins include but not limited to Ig-like, actinoporin-like, β-trefoil pore forming lectins, galectin, 6bladed β-propeller, and 7-bladed β-propeller, and any other types of know or unknown pathogen lectins.

Animal glycan-recognizing proteins including but not limited to two groups—lectins and sulfated glycosaminoglycan (SGAG)-binding proteins. The biosynthesis of structurally complex GAG is regulated and its diverse sulfation pattern is formed organ- and tissue-specifically as well as temporally during growth and development. Proteins other than antibodies and T-cell receptors that mediate glycan recognition via immunoglobulin (Ig)-like domains are called "I-type lectins." The major homologous subfamily of I-type lectins with sialic acid (Sia)-binding properties and characteristic amino-terminal structural features are called the "Siglecs" (Sia-recognizing Ig-superfamily lectins).

Mucins can be sialic acid-containing glycoproteins. Mucins are secreted in the mucus of the respiratory and digestive tracts. Mucin genes encode mucin monomers that are synthesized as rod-shape apomucin cores that are post-translationally modified by exceptionally abundant glycosylation. Two distinctly different regions are found in mature mucins: 1) The amino- and carboxy-terminal regions are very lightly glycosylated, but rich in cysteines, which are likely involved in establishing disulfide linkages within and among mucin monomers. 2) A large central region formed of multiple tandem repeats of 10 to 80 residue sequences in which up to half of the amino acids are serine or threonine. This area becomes saturated with hundreds of O-linked oligosaccharides. N-linked oligosaccharides are also found on mucins, but much less abundantly. At least 19 human mucin genes have been distinguished by cDNA cloning—MUC1, 2, 3A, 3B, 4, 5AC, 5B, 6-9, 11-13, and 15-19. The major secreted airway mucins are MUC5AC and MUC5B, while MUC2 is secreted mostly in the intestine but also in the airway. Increased mucin production occurs in many adenocarcinomas, including cancer of the pancreas, lung, breast, ovary, colon, etc. Mucins are also over expressed in lung diseases such as asthma, bronchitis, COPD or cystic fibrosis.

Herbs and Traditional Chinese Herbs

As used herein, an herb refers to a plant that is valued for qualities such as medicinal properties, flavor, scent, or the like. In the present disclosure, traditional Chinese herbs include but not limited to all herbs listed in Bencao Gangmu (traditional Chinese: simplified Chinese: pinyin: BěncǎoGāngmù; Wade-Giles: Pen-ts'ao Kang-mu), also known as Compendium of Materia Medica, which is Chinese materia medica work written by Li Shizhen in Ming Dynasty. It is a work epitomizing materia medica in Ming Dynasty. It lists all the plants, animals, minerals, and other objects that were believed to have medicinal properties.

Specifically, fundamental traditional Chinese herbs include but not limited to: *Agastache rugosa*—huò xiāng, *Alangium chinense*—bā jiǎofēng, *Anemone chinensis* (syn. *Pulsatilla chinensis*)—bái tóu weng, *Anisodus tanguticus*—shān láng dáng, *Ardisia japonica*—zǐ jīn niú, *Aster tataricus*—zǐ wǎn, *Astragalus propinquus* (syn. *Astragalus membranaceus*)—huáng qi or běi qi, *Camellia sinensis*—chá shù or cháyè, *Cannabis sativa*—dàmá, *Carthamus tinctorius*—hóng huā, *Cinnamomum cassia*—ròu guì, *Cissampelos pareira*—xí shēng téng, *Coptis chinensis*—duǎn è huáng lián, *Corydalis ambigua*—yán hú suǒ, *Croton tiglium*—bā dòu, *Daphne genkwa*—yuán huā, *Datura metel*—yáng jīn huā, *Datura stramonium* (syn. *Datura tatula*)[13]—zǐ huā màn tuó luó, *Dendrobium nobile* shí hú or shí hú lán, *Dichroa febrifuga*[14]—cháng shān, *Ephedra sinica*—cǎo má huáng, *Eucommia ulmoides*—dù zhòng, *Euphorbia pekinensis* [15]—dàjǐ, *Flueggea suffruticosa* (formerly *Securinega suffruticosa*)—yī yè qiū, *Forsythia suspensa* liánqiào, *Gentiana loureiroi*—dì dīng, *Gleditsia sinensis*—zào jiá, *Glycyrrhiza uralensis*—gāncǎo, *Hydnocarpus anthelminticus* (syn. *H. anthelminthica*)—dà fēng zǐ, *Ilex purpurea*—dōngqīng, *Leonurus japonicus*—yì mǔ cǎo, *Ligusticum wallichii*[18]—chuān xiōng, *Lobelia chinensis*—bàn biān lián, *Phellodendron amurense*—huáng bǎi, *Platycladus orientalis* (formerly *Thuja orientalis*)—cèbǎi, *Pseudolarix amabilis*—jīn qián sōng, *Psilopeganum sinense*—shān má huáng, *Pueraria lobata*—gé gēn, *Rauwolfia serpentina*—shégēnmù, cóng shégēnmù, or yìndù shé mù, *Rehmannia glutinosa*—dihuáng or gān dihuáng-, *Rheum officinale*—yào yòng dà huáng, *Rhododendron* tsinghaiense—Qīng hǎi dù juān, *Saussurea costus*—yún mù xi āng, *Schisandra chinensis*—wǔ wèi zi, *Scutellaria baicalensis*—huáng qín, *Stemona tuberosa*—bǎi bù, *Stephania tetrandra* fáng ji, *Styphnolobium japonicum* (formerly *Sophora japonica*)—huái, huái shù, or huái huā, *Trichosanthes kirilowii*—guā lóu, and *Wikstroemia indica*—liǎogē wáng, *Isatis indigotica*—ban lan gen, Yun nan bai yao, *Eclipta* prostrate herb dan shen, *Taraxacum mongolicum* herb—pu gong ying, *Ginseng*—ren shen, *Rehmannia glutinosa*/foxglove root prep.—shu di huang, Panta Teapills— jiao gu lan, *Dioscorea* opposite/Chinese yam rhizome—shan yao, *Paeonia suffruticosa*/peony tree root-bark—mu dan pi, *Poria cocos* fungus/mushroom filaments—fu ling, *Alisma plantago aquatica*/water plantain rhizome—Ze xie, *Cornus officinalis*/dogwood tree fruit—shan zhu yu, *Cinnamomum cassia*/cinnamon bark—rou gui, *Aconitum carmichaeli* root prep. —Shu fu zi, *Codonopsis* root—dang shen, Eleuthro root—ci wu jia, *Cordyceps*—dong chong xia cao, Reshi/Mushroom of Immortality—ling zhi, *Polygonum multiflorum* root, *Coix* lachrymal jobi/Seeds of Jobs Ears seed—yi yi ren, *Cinnamomum cassia*/cinnamon twig—gui zhi, *Zingiber* officinal rhizome. Ginger root—sheng jiang, *Paeonia lactiflora*/white peony root—bai shao, *Angelica sinensis* root dang gui, *Ledebouriella divaricata* root—fang feng, *Poria cocos* fungus—fuling, *Eucommia ulmoides* bark—du zhong, *Atractylodes lancea* rhizome e-cang zhu, *Platycodon grandiflorum*/ballon flower root—jie geng, *Boswellia carterii*—ru xiang, *Commiphora myrrha*/myrrh resin—mo yao, *Corydalis yanhusuo*/fumewort rhizome—yan hu suo, *Prunus persica*/peach seed—tao ren, Deer antler—lu rong, *Atractylodes macrocephala*—bai zhu, *Mentha* halocalyx/field mint hearb—bohe, *Bupleurum chinense* root—chai hu, Forsythisia suspense fruit—lian qiao, *Angelica dahurica* root bai zhi, *Citrus reticulate*/citrus peel—chen pi, *Ziziphus* jujube/Chinese date fruit—da zao, *Chrysanthemum morifolium* flower—ju hua, *Ziziphus spinosa*/sour jujube seed suan zao ren, *Dioscorea* opposite/Chinese yam rhizome—shanyao, Buckwheat—qiao mai, *Pinellia ternata* rhizome—ban xia.

Inorganic Ions and Small Molecules

The inorganic ions in the present disclosure include mineral nutrients that include but not limited to elements boron, copper, manganese, zinc, molybdenum, sulphur, iron, calcium, potassium, nitrate, phosphate, chloride, etc., without limitation. The small molecules in the present disclosure include but not limited to glycan binding peptides, carbohydrate chains which are also called aliphatic hydrocarbons and have the collective formula $C_nH_{n+2}$; structural isomers which share the same hydrocarbon formula but have different structures; unsaturated hydrocarbons in which carbohydrate chains containing multiple bonds; alcohols which are aliphatic carbon compounds that carry on or more hydroxyl-groups directly linked to a carbon atom; aldehydes that of secondary alcohols to ketones; organic acid which are produced by the oxidation of an aldehyde group; esters which are produced by a condensation reaction of an alcohol and an acid, or any other known or unknown small molecules, without limitation.

Toxins

The toxins in the present disclosure include but not limited to apitoxin, exotoxin, endotoxins, cyanotoxins, necrotoxins, hemotoxin, mycotoxin, neurotoxin, phototoxin, toxicophore, toxoid, venom, ricinis, or any other known or unknown toxins, without limitation.

A toxin is a poisonous substance produced by living cells or organisms that is active at very low concentrations. Toxins can be small molecules, peptides, or proteins and are capable of causing disease on contact or absorption with body tissues by interacting with biological macromolecules such as enzymes or cellular receptors. Toxins vary greatly in their severity, ranging from usually minor and acute (as in a bee sting) to almost immediately deadly (as in botulinum toxin). Biotoxins vary greatly in purpose and mechanism, and can be highly complex (the venom of the cone snail contains dozens of small proteins, each targeting a specific nerve channel or receptor), or relatively small protein.

Primary Screening

The materials and chemicals for primary screening as described above can be used as either targets or detection reagents in the process of primary screen. They are called "target candidate" or "detection candidate" hereafter.

Target Candidates

Target candidates can be attached or fixed on to a carrier as mentioned above in various combinations depending on needs. The combinations of target and detection candidates include but not limited to those listed in Table 1.

TABLE 1

Combinations of target and detection candidate binding

| | Targets | | | | | | | |
|---|---|---|---|---|---|---|---|---|
| Detection | Antibodies | Glycans | Lectins/GRS | Pathogens | Herbs | Small molecules | Toxins | Cells/Tissues |
| Antibodies |  | + | + | + | + | + | + | + |
| Glycans | + |  | + | + | + | + | + | + |
| Lectins/GRS | + | + |  | + | + | + | + | + |
| Pathogens | + | + | + |  |  | + | + | + |
| Herbs | + | + | + | + |  | + | + | + |
| Small molecules | + | + | + | + | + |  | + | + |
| Toxins | + | + | + | + | + | + |  | + |
| Cells/Tissues | + | + | + | + | + | + | + |  |

Note:
Glycans include glycans and glycan conjugates,
GRS = Glycan Recognition Systems In table 1, tissues include but not limited to various healthy and disease cells and tissues 10 of organisms and herbs include but not limited to traditional Chinese herbs, as described above. The symbol "+" means binding of two candidates.

Type I: Target candidates include glycans, pathogens and healthy tissues. Glycans include at least but not limited to fructose, glucose (Glc), mannose (Man), fucose (Fuc), xylose (Xyl), galactose (Gal), lactose, glucosamine (GlcN), galactosamine (GalN), mannosamine (ManN), N-Acetylglucosamine (GlcNAc), N-Acetylgalactosamine (GalNAc), N-Acetylmannosamine (ManNAc), N-Acetylneuraminic acid (NeuSAc), N-Glycolylneuraminic acid (Neu5Gc), 2Keto-3-deoxynononic acid (Kdn), glucuronic acid (GlcA), galacturonic acid (GalA), mannuronic acid (ManA), and Iduronic acid (IdoA). Healthy tissues include but not limited to various cells or tissues from at least one healthy organism include but not limited to humans, animals, plants, or other organisms.

Detection candidates for binding to the Type-I target candidates include but not limited to glycans, antibodies, lectins including plant lectins or other glycan recognition systems, herbs, small molecules or toxins, depending on needs.

Type II: Target candidates include glycans (as described in Type I), pathogens and disease tissues. Disease tissues include but not limited to various cells or tissues from at least one organism with at least one of infectious diseases, cancers, autoimmune diseases, allergies, toxicity, obesity or other disorders. Detection candidates are as same as described in Type I.

Type III: Target candidates include glycans, pathogens, healthy and disease tissues (as described in Type I and Type II). Detection candidates are as same as described in Type I.

Type IV: Target candidates include at least one kind of target candidates including but not limited to antibodies, lectins including plant lectins or other glycan recognition systems, herbs, small molecules and toxins, depending on needs.

Detection candidates include but not limited to glycans, pathogens, and extracts or homogenates or lysates of healthy or diseased cells or tissues or organs of an organism, depending on needs.

Type V: Target candidates include any two kinds of target candidates as described in type IV. Detection candidates are as same as described in type IV.

Type VI: Target candidates include any three kinds of target candidates as described in type IV. Detection candidates are as same as described in type IV.

Type VII: Target candidates include any four kinds of target as described in type IV. Detection candidates are as same as described in type IV.

Type VIII: Target candidates include antibodies, lectins including plant lectins or other glycan recognition systems, herbs, small molecules and toxins. Detection candidates are as same as described in type IV.

Other combinations of target and detection candidates depending on needs are also included.

Binding of Detection Candidates to Target Candidates

One aspect of the present disclosure relates to binding of a detection candidate to an array carrier with at least one combination of target candidates as mentioned above. The detection candidate can be either purified or conjugated with a moiety such as biotin, fluorescents or any other detectable means known in the art. A secondary or third reagent can be used if necessary for the detection of the candidate/carrier binding in various ways known in the art.

The patterns of a detection candidate binding to the target candidates on an array carrier include but not limited to follows.

Type I-III Assays

Type I, Type II, and Type III arrays are useful tools for the rapid identification of antigens in one organism that mimic with antigens of at least another organism especially pathogenic organisms or infectious agents; and determine the nature of the therapeutic targets. Examples include:

a. A glycan binds to at least one pathogen: the glycan is a potential biding site of the pathogen, and any healthy and/or disease tissues of an organism with the glycan as part of their cells or tissues structures can be the target of the pathogen. The pathogen is the potential cause of the disorders relevant to these tissues or organs.

b. A glycan binds to more than one pathogen: the pathogens and the glycan are candidates for binding site-, or receptor/ligand-, or anti-multiple pathogen-vaccines.

c. A detection candidate binds to at least one pathogen and at least one healthy and/or disease tissues of an organism: there is a therapeutic target sharing by the pathogen and the tissue.

Figure 2:
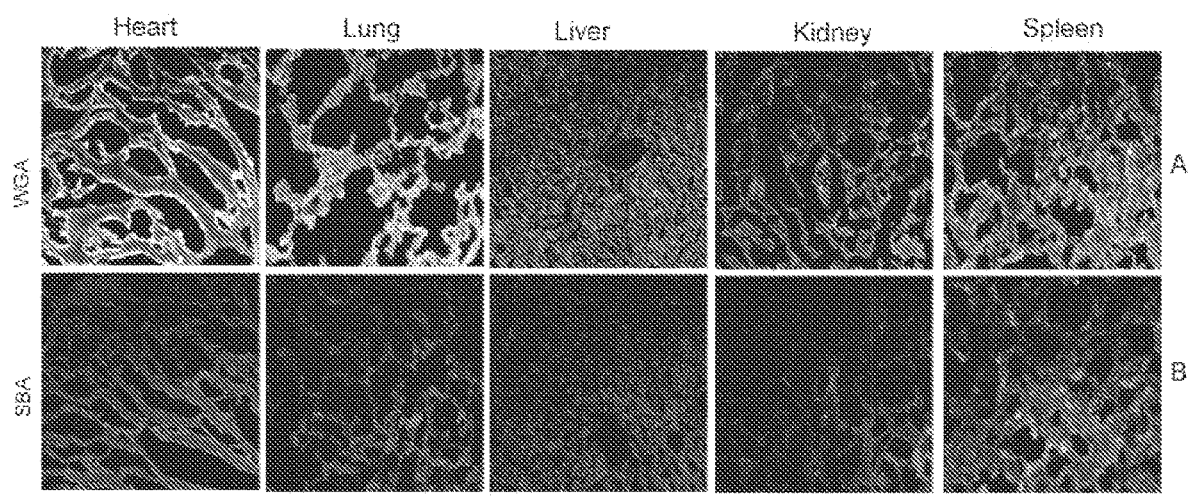
FIG. 2 is a graphical representation of binding of plant lectins of WGA and soybean agglutinin (SBA) to tissue sections of adult mice.
Figure 3:
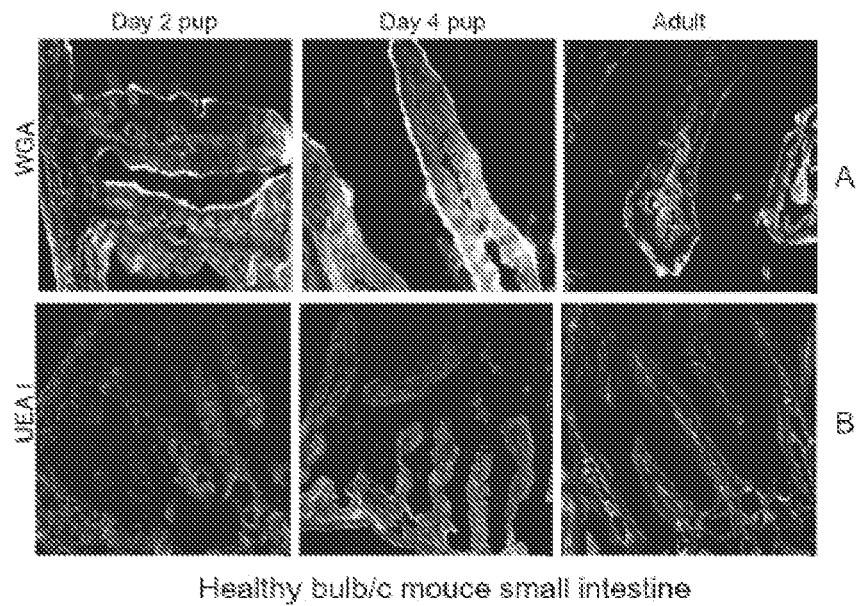
FIG. 3 is a graphical representation of binding of plant lectins of wheat germ agglutinin (WGA) and *Ulex Europaeus* agglutinin I (UEA I) to tissue section of small intestine of healthy newborn pups and adult mice.

If the detection candidate is an antibody against a pathogen, the pathogen and the antibody are potential causes of an autoimmune disease, an allergy, a toxin-relevant biological injury or another disease targeting the tissue or organ. The antibody is a potential candidate for diagnosis, antibody prevention and therapy, drug delivery tool of the relevant disorders. For example, an anti-rotavirus (RV) antibody binds to N-Acetyl-D-Glucosamine which is expressed on heart, lung and small intestine of healthy mice (FIG. 2 and FIG. 3) and inflammatory (FIG. 4) or proliferating (FIG. 5) cells. Thus, anti-RV antibodies can be an inflammatory inducer and a cause of autoimmune diseases or cancers of those tissues or organs.

If the detection candidate is a glycan, a plant lectin (i.e., mannose-binding lectin) or another glycan recognition systems, a herb, a small molecule or a toxin, the detection candidate is a potential cause of an autoimmune disease, an allergy, a toxin-relevant biological injury or another disease targeting the tissue or organ; or a potential candidate for diagnosis, prevention, therapy, drug and drug delivery tool of the relevant disorders. For example, wheat germ agglutinin (WGA) which specifically recognizes N-Acetyl-D-Glucosamine can be a cause of the disorders of the tissues or organs expressing N-Acetyl-D-Glucosamine.

d. A candidate binds to at least one pathogen, at least one healthy and/or diseased tissue of an organism and at least one glycan: the glycan is the potential epitope of the therapeutic target sharing by the pathogen and the tissue. The glycan and its derivatives are potential causes of disorders relevant to the therapeutic target, or potential candidates for diagnosis, prevention, therapy, drug and drug delivery tool of the relevant disorders.

Type IV-VIII Arrays

Type IV, Type V, Type IV, Type-VII and Type-VIII arrays are useful tools for the rapid screening of causes, drugs and drug delivery tools for diagnosis, prevention and therapy of the disorders relevant to the a therapeutic target and/or a pathogen. Examples include:

a. A target candidate of Type IV-VIII arrays is bound by a glycan: the target candidate is a potential cause of disorders relevant to a therapeutic target with the glycan as an epitope; and the target candidate can be used for diagnosis, prevention, therapy, drug and drug delivery tool of the disorders relevant to the therapeutic target.

b. A target candidate of Type IV-VIII arrays is bound by a pathogen (i.e., a virus): the target candidate is a potential candidate for diagnosis, prevention, therapy, drug and drug delivery tool of the disorders relevant to the pathogen.

c. A target candidate of Type IV-VIII arrays is bound by an extracts or homogenates or lysates of healthy or diseased cells or tissues or organs of an organism: the target candidate is a potential candidate for diagnosis, prevention, therapy, drug and drug delivery tool of the disorders relevant to the cell or tissue or organ of the organism.

d. A glycan binds to at least two different antibodies against different pathogens (i.e., antibodies against RSV and antibodies against influenza viruses): the pathogens are candidates for binding site- or anti-multiple pathogen-vaccines.

e. A pathogen (i.e., RSV) binds to more than one antibodies against different pathogens (i.e., antibodies against RSV and antibodies against influenza viruses): the pathogens are candidates for binding site-, or receptor/ligand-, or multiple pathogen-vaccines.

Other arrays with other combinations of target and detection candidates depending on needs are also included.

Purification and Identification of a Therapeutic Target

A biological target in one embodiment is a biopolymer such as a protein or nucleic acid whose activity can be modified by an external stimulus. The definition is context-dependent and can refer to the biological target of a pharmacologically active drug compound, or the receptor target of a hormone (like insulin). The implication is that a molecule is "hit" by a signal and its behavior is thereby changed. Biological targets are most commonly proteins such as enzymes, ion channels, and receptors. The term biological target is frequently used in pharmaceutical research to describe the native protein in the body whose activity is modified by a drug resulting in a desirable therapeutic effect. In this context, the biological target is often referred to as a drug target. A biomarker is a substance used as an indicator of a biologic state. It is a characteristic that is objectively measured and evaluated as an indicator of normal biologic processes, pathogenic processes, or pharmacologic responses to a therapeutic intervention. In the present disclosure, a therapeutic target includes but not limited to a biological target, a drug target, a biomarker, and a pathogen binding site, which is related to a disorder of an organism.

In another embodiment, a simple method for identification of a functionally important therapeutic target comprises using a selected candidate (i.e., an antibody preferably monoclonal antibody against a pathogen). This approach may eliminate laborious screening work for an interested antigen as regularly used in the field of protein purification. According to the present disclosure, sera, lysates or extract of available related cells, tissues and/or organs of humans, animals or plants as mentioned above, can be used for purification of a therapeutic target in a variety of ways well known to those of ordinary skill in the art.

Identification of the sequence or structure of a therapeutic target, key molecules being related to the binding of a therapeutic target and a given candidate, derivatives of a therapeutic target in a variety of ways well known to those of ordinary skill in the art is also included in the present disclosure.

The therapeutic targets according to the present disclosure can be a glycoprotein; glycan; polypeptides; polysaccharides; oligosaccharides; lipid, glycolipid; carbohydrate; lectin, selectin; mucin; hemagglutinin, collagen, keratin, receptor including viral receptors, toll-like receptor; cellular component; oncogene product; fragments of mammalian cells there from including tumor cells, or any other substance without limitation.

A feature of the therapeutic targets according to one embodiment of the present disclosure is that a therapeutic target can be either preventive or pathogenic depending on the features of the target as described herein.

Cellular or Tissue Culture Assays and Animal Experiments

In one embodiment, a candidate showing positive binding in the primary screening may be subject to following process.

Cellular or Tissue Culture Assays

According to one embodiment of the present disclosure, a cell or tissue culture assay can be used to determine the functional and pathogenic characteristics of a selected candidate or a combination of at least two selected candidates.

That is whether a target or detection candidate is a binding site of a pathogen, or whether a target or detection candidate induces significant biological disorders. The cell or tissue culture assay can be also used to determine the pharmacological, kinetics, and toxic effect of a selected candidate or a combination of at least two candidates determined through the primary screening of an array. Examples include:

a. Cell lines sensitive to infectious pathogens known in the art, and also primary healthy cells or tissues or organs (i.e., targets of viral infectious diseases) can be cultured with a selected candidate or a combination of at least two selected candidates at various dosages for a period time sufficient for the candidate to bind to its target existing on the cells or tissues or organs, the free candidate not binding to the target should be washed off, and the cells or tissues or organs are treated with the pathogen (i.e., a virus strain) for a period time sufficient for the pathogen to enter into the target cells. The infection of the pathogen can be detected in a variety of ways well known to those of ordinary skill in the art (i.e., determination of the titer of a virus strain in the culture supernatant).

Alternatively, the same cellular or tissue culture system can be cultured with an infectious pathogen at a given dosages for a period time sufficient for the pathogen enter into the target cells, the free pathogen remaining in the culture should be washed off, and the cells or tissues or organs are cultured with a selected candidate or a combination of at least two selected candidates at various dosages. The infection of the pathogen can be detected as described above.

In the case that the target is the binding site or factors related to the entry or infection of the pathogen, the selected candidate or the combination of at least two selected candidates can block the target and prevent the entry or infection of the pathogen into the cells or tissues or organs. Thereof the cells or tissues or organs with treatment of the selected candidate or the combination of at least two selected candidates before and after infection will not be or lightly infected by the pathogen. This method can be also used for rapid discovery of drugs and drug delivery systems relevant to infectious diseases.

b. The same cellular or tissue culture system as described above in 'a' can be cultured with a selected candidate or a combination of at least two selected candidates alone at various dosages for a period time. The effect of a candidate a combination of at least two candidates on cellular proliferation, signal transduction, apoptosis, necrosis, and other functions of the cells or tissues or organs can be determined in a variety of ways well known to those of ordinary skill in the art.

This method can be used for the functional and pathogenesis studies of a combination of at least two selected candidates, as well as cause screening of autoimmune diseases, allergies, inflammation, toxicity cancers, obesity and other disorders; for toxic, pharmacological and pharmaceutical studies of a selected candidate; for rapid discovery of target-based drugs and drug delivery systems relevant to those disorders.

c. Disease cell lines known in the art (i.e., cell lines derived from tumor tissues), and also primary disease cells or tissues or organs (i.e., tumor cells or tissues) can be cultured with a selected candidate or a combination of at least two selected candidates at various dosages for a period time. The effect of the candidate or the combination of the at least two candidates on cellular proliferation, signal transduction, apoptosis, necrosis, and other functions of the disease cells or tissues or organs can be determined in a variety of ways well known to those of ordinary skill in the art.

This method can be used for the pathogenesis studies of a selected candidate or a combination of at least two selected candidates, as well as cause screening of autoimmune diseases, allergies, cancers, inflammation, obesity and other disorders; for toxic, pharmacological and pharmaceutical studies of a selected candidate or a combination of at least two selected candidates; for rapid discovery of target-based drugs and drug delivery systems relevant to those disorders.

Animal Experiments

Another subject of the present disclosure is the use of animal experiments to determine the functional and pathogenic characteristics of a selected target or a combination of at least two selected candidates. That is whether a therapeutic target is a binding site of a pathogen, or whether a therapeutic target induces significant biological disorders in an organism. Animals at various ages (i.e., embryo, fetus, newborn, infant and adult) can be used to evaluate characteristics of therapeutic targets with a strong expression pattern in the embryo or fetus that decreases with growth.

The animal experiments can be also used to determine the pharmacological and toxic effect of a candidate or a combination of at least two candidates determined through the primary screening for rapid discovery of target-based drugs and drug delivery systems relevant to infectious diseases, autoimmune diseases, allergies, cancers, inflammation, toxicity, obesity, and other disorders.

All involved animals are checked daily for symptoms of a disorder, death, etc. Blood and the target and control organs or tissues of the animals (determined in primary screening) are collected at determined time point (i.e., day 1, 3, 5, 7, 14, 21, 28 after a treatment). The collected samples are used to evaluate the effect of a candidate or a combination of at least two candidates on inflammation, pathogenesis, toxicity, cellular proliferation, signal transduction, apoptosis, necrosis, and other functions of the target tissues or organs of the animal in a variety of ways well known to those of ordinary skill in the art (i.e., histology changes). Animals being treated with candidates are also compared to control animals without candidate treating for detection of pathogens and/or binding of candidates to target tissues and/or organs. Examples include:

a. A selected candidate or a combination of at least two selected candidates can be administered to an animal (i.e., a mouse) for a period of time sufficient for the candidate or the combination of the at least two candidates to bind to or interact with the target of the animal. The animal is then challenged by the pathogen (i.e., a virus). In the case that the target is the binding site or factors related to the entry of the pathogen, the candidate or the combination of the at least two candidates can block or affect the binding site and prevent the entry of the pathogen into the target cells of the animal. Thereof the animal will not be or lightly affected by the pathogen. The same animal model can also be used to determine the therapeutic effect of the selected candidate or the combination of the at least two candidates on the relevant disease by administering a selected candidate or a combination of at least two candidates to an animal after the challenge of the pathogen. Animals such as mice can be treated with the candidate or the combination of the at least two candidates at a low dosage within the range that yields efficacy of blocking without much extras, with the ordinary skill in the art; virus inoculation can be performed next day. The selected candidate or the combination of the at least two candidates can be also administered one day after virus inoculation. Rest of experiments including evaluate symptoms of infection, determining viral titers can be performed in the ordinary skill in the art.

b. Alternatively, the same animal can be treated by a selected candidate or a combination of at least two selected candidates alone at various dosages. A selective candidate or a combination of at least two selected candidates can be administered intravenously, intraperitoneally, intramuscularly, subcutaneously, intracavity, transdermally, inhalantly or with other approaches. A selective candidate or a combination of at least two selected candidates can be administered into a pregnant animal and be detected in the newborns or infants delivered to the mother. If administration of a selected candidate a combination of at least two selected candidates alone induces a significant biological disorder in an animal, the target and the candidate is identified as pathogenic, and the animal can be used as an experimental model for the disorder.

c. Binding of a candidate to cells or tissues or organs in vivo can be detected using the tissues collected from the animals treated with the candidate alone. The binding candidates usable in the present disclosure can be also used for in vivo imaging, wherein for example a selective candidate labeled with a detectable moiety is administered to a human or an animal, preferably into the bloodstream, and the presence and location of the labeled candidate in the host is detected. The candidate can be labeled with any moiety that is detectable in human and/or animals whether by nuclear magnetic resonance, radiology, fluorescence, or other detection means known in the art.

d. Combination of in vivo and in vitro methods of candidate binding and detection as mentioned above can be also used preferably in animals. For example, a selected candidate labeled with a moiety can be administered to an animal, the candidate can bind to or interact with its target in vivo, followed by scarification of the animal, collection of tissue or organ samples and detection of the bound candidate in vitro using detection means known in the art.

e. Embryo culture system An organism embryo (i.e., chicken or zebra fish) culture system can be used to detect the inhibitory effect of candidates against pathogens (i.e., viruses). A middle term embryo is treated with at least one selected candidate or one combination of at least two selected candidates at a low dosage within the range that yields efficacy of blocking or acting without much extras, in the ordinary skill in the art; pathogen inoculation can be performed next day. Candidates can be also administrated one day after pathogen inoculation. Rest of experiments including harvesting fluid containing pathogens, determining pathogen titers can be performed in the ordinary skill in the art. Lower pathogen tiers from an embryo culture being treated with a candidate or one combination of at least two candidates compared to controls without candidate treating can indicate an efficacy of prevention or therapy.

Other cellular or tissue culture and animal experiments depending on needs are also included.

Features or Characteristics of Therapeutic Targets

Based on the results of cellular or tissue culture and animal experiments as described above, the features or characteristics and utilities of therapeutic targets include but not limited to the following:

Type A: A therapeutic target is the binding site of a pathogen but not a pathogenic site (the therapeutic target does not induce significant biological disorders in an organism).

This therapeutic target can be the receptor of the antibodies induced by an effective vaccine and an effective passive immunity without significant side effects, and should be the goal of vaccine development and antibody prevention and therapy. The therapeutic target is also a good candidate of immunogen for a binding-site vaccine. The agonists and other derivatives of the therapeutic target are good candidates for the prevention, treatment and drug delivery tools of the diseases relevant to the target (i.e., a viral infection).

A candidate capable of binding to the therapeutic target as described above can be directly used as drugs for prevention, therapy and drug delivery tool of the relevant disorder.

Type B: A therapeutic target is the binding site of a pathogen and a pathogenic site (the therapeutic target induces significant biological disorders in an organism).

This type of therapeutic target can be the receptor of the antibodies induced by an effective vaccine and an effective passive immunity with significant side effects. The vaccine and antibody prevention and therapy should be administrated carefully. That is, efficacy for the blocking of pathogen binding sites should be sought while trying to minimize any extra free antibodies. The antagonists and other derivatives of the therapeutic target are good candidates for the prevention, treatment and drug delivery tools of the diseases relevant to the antigen (i.e., a viral infection).

Candidates capable of binding to the therapeutic target as described above can be the causes of inflammation, autoimmune diseases, allergy, cancers, obesity and other disorders. These candidates can be used as drugs for diagnosis of these disorders, therapy and drug delivery tool of the relevant disorder either at low dose or conjugated with an antagonist or inhibitor of the therapeutic target. These candidates can also be used for development of animal models of the relevant disorders.

Type C: A therapeutic target is not the binding site of a pathogen but a pathogenic site (induces significant side effects, toxicity or disorders).

This type of therapeutic target should be avoided in vaccine development. Candidates capable of binding to this type of therapeutic target can be the causes of bio toxicity, pathogenic mechanisms of diseases with high death rates (i.e., avian influenza and Ebola virus infection), autoimmune diseases, allergy, cancers, inflammation, obesity and other disorders. These candidates can be used for diagnosis of these disorders, and should be avoided in direct use for the treatment of the relevant disorders. However, these candidates can be used as drugs for therapy and as drug delivery tools of the relevant disorders by conjugation with an antagonist or inhibitor of the therapeutic target. On the other hand, these candidates can be used for development of animal models of the relevant disorders.

Type D: A target is neither the binding site of a pathogen nor a pathogenic site. This type of therapeutic target can be the cause of a vaccine's ineffectiveness and should be avoided in vaccine development.

Candidates capable of binding to this type of therapeutic targets should be avoided for all applications in an organism except as a drug delivery tool if such a binding is organ and/or tissue specific.

Binding site-based new therapeutics for prevention and treatment of an infection can be achieved based on following mechanisms: 1) to compete with the pathogen binding site. 2) to block the pathogen binding site. 3) to modify the chemical nature of the pathogen binding site.

Pathogenic site-based new therapeutics for prevention and treatment of infections, cancers, autoimmune diseases, allergy, inflammation, obesity and other disorders can be achieved based on following mechanisms: 1) to inhibit the pathogenic site; 2) to neutralize or compete with the pathogenic inducer; and 3) to modify the chemical nature of the pathogenic site.

Numerous other features or characteristics of therapeutic targets can become readily apparent from the detailed description.

Utilities of Glycan-Based Array

Glycan-based array and the therapeutic targets identified by a glycan-based array according to the present disclosure have several utilities as described herein, including utility suitable for humans, animals, plants and other organisms, such as: 1) The rapid identification of therapeutic targets; 2) The pathogenesis studies and cause screening of infectious diseases, autoimmune diseases, allergies, toxicity, cancers, obesity and other disorders; 3) The development of animal models of autoimmune diseases, allergies, toxicity, cancers, obesity and other disorders; 4) The development of high quality and new vaccines (i.e., binding site-based vaccines); 5) The effective control of pandemic diseases (i.e., binding site-based prevention and therapy); 6) The functional, toxic, pharmacological and pharmaceutical studies of plant lectins, herbs, toxins and small molecules; 7) The rapid discovery of drugs and drug delivery systems relevant to therapeutic targets; 8) The application of therapeutic targets, their derivatives and any other forms of the therapeutic targets for the diagnosis, prevention, treatment and drug delivery of infectious diseases, autoimmune diseases, allergies, cancers, obesity and other disorders related to at least one therapeutic target; 9) The studies of epidemiology and biology especially evolutionary biology; and 10) Numerous other utilities of molecular mimicry array can become readily apparent from the detailed description in current disclosure and PCT/US2007/018258.

Glycan-Related Therapeutic Targets and Infectious Diseases

In one embodiment of the present disclosure, a useful tool is provided for understanding the etiology, pathogenesis, treatment, and prevention of infectious diseases as described in PCT/US2007/018258.

In addition, small animal models for HIV infection can be developed based on the new organ tropism of HIV (i.e., mouse intestine). Small animals include but not limited to mouse, rat, guinea pig, rabbit, etc. Animals are infected with either viable or inactivated HIV followed by detection of HIV in the tropic organs (i.e., mouse intestine).

Glycan-Related Therapeutic Targets and Inflammation, Autoimmune Disorders and Allergies In another embodiment of the present disclosure, a useful tool is provided for understanding the etiology, pathogenesis, treatment, and prevention of autoimmune disorders as described in PCT/US2007/018258.

In addition, antibodies and other candidates as described in the current disclosure can be also used for diagnosis, prevention and treatment of inflammation, cancers, autoimmune disorders and allergies with the similar methods as described in PCT/US2007/018258.

Glycan-Related Therapeutic Targets and Cancers, Obesity, and Other Disorders

In yet another embodiment of the present disclosure, a useful tool is provided for understanding the etiology, pathogenesis, treatment, and prevention of cancers, obesity, and other disorders as described in PCT/US2007/018258.

In addition, antibodies and other candidates as described in the current disclosure can be also used for diagnosis, prevention and treatment of inflammation, autoimmune disorders and allergies and other disorders using the similar methods as described in PCT/US2007/018258.

The Mechanisms of Vaccination and Passive Immunity and New Vaccines

In another embodiment of the present disclosure, a useful tool is provided for understanding the mechanisms of vaccination and passive immunity and development of new and high quality vaccines as described in PCT/US2007/018258.

In addition, the candidates as described in the current disclosure can be used to develop binding-site vaccines as well as anti-multi-pathogen vaccines. Evaluation of the binding site features of the antibodies induced by a vaccine is critically important to judge whether a vaccine is good or not.

Therapeutic Target-Based Prevention and Treatment

The present disclosure also extends to a strategy for developing novel methods of prevention, diagnosis, and treatment of the relevant disorders, obtainable based on the therapeutic target being identified, including, but not limited to methods suitable for humans, animals, plants and other organisms.

As described in PCT/US2007/018258 and the current disclosure, candidates (including antibodies) related to therapeutic targets existing in organisms including humans or animals can be used for the diagnosis, prevention (therapeutic target-based prevention) and treatment (therapeutic target-based therapy) of infectious diseases, autoimmune disorders, allergies, cancers, inflammation, obesity, and other disorders. In addition, such candidates can be also used as drug delivery tools for treatment of infectious diseases, autoimmune disorders, allergies, cancers, inflammation, obesity, and other disorders.

Another strategy would be to use the derivatives of therapeutic targets for the diagnosis, prevention and treatment of infectious diseases, autoimmune disorders, allergies, cancers, inflammation, obesity, and other disorders using the similar methods as described in PCT/US2007/018258 and the current disclosure.

In addition, derivatives of therapeutic targets can be also used as drug delivery tools for treatment of infectious diseases, autoimmune disorders, allergies, cancers, inflammation, obesity, and other disorders.

Another subject of the present disclosure is the use of inactivated particles or fragments or extracts of a pathogenic reagent which shares a therapeutic target with a biological organism for the prevention and treatment of the related infectious diseases, autoimmune disorders, allergies, cancers, inflammation, obesity, and other disorders as described PCT/US2007/018258 and the current disclosure.

In addition, inactivated particles or fragments or extracts of a pathogen can be also used as drug delivery tools for treatment of infectious diseases, autoimmune disorders, allergies, cancers, inflammation, obesity, and other disorders.

Another subject of the present disclosure is the use of a pathogenically therapeutic target and/or its relevant candidates and/or its derivatives which causes an autoimmune disease for diagnosis of the autoimmune disease, cancers and other related disorders. Kits containing pathogens or therapeutic targets obtained through the process of the present disclosure and/or antibodies to the pathogens or therapeutic targets can be prepared in a variety of ways well known to those of ordinary skill in the art. Such kits are used to detect the presence of the antibody to the antigen in a biological sample.

According to the present disclosure, pharmaceutically useful compositions comprising the therapeutic targets and/or its derivatives or any other relevant candidates of the therapeutic target can be formulated, according to known methods such as by the admixture of a pharmaceutically acceptable carrier. Such compositions can contain an effective amount of the antigens or other forms of the antigen and/or its relevant candidates or any other relevant candidates of the therapeutic target to form a pharmaceutically acceptable composition suitable for effective administration.

The dosage regimen utilizing the therapeutic targets and/or its derivatives or any other relevant candidates of the therapeutic target according to the present disclosure is selected in accordance with a variety of factors including location and density of the antigen, type, species, age, weight, sex and medical condition of the patient; the severity of the condition to be treated; the route of administration; the renal and hepatic function of the patient; and the particular substances thereof employed. Optimal precision in achieving concentrations of the said substances of the present disclosure within the range that yields efficacy without toxicity requires a regimen based on the kinetics of the thereof employed substance availability to target sites. This involves a consideration of the distribution, equilibrium, and elimination of the thereof employed substances of the present disclosure.

The present disclosure also has in one embodiment the objective of providing suitable topical, oral systemic and parenteral pharmaceutical formulations for use in the novel methods of prevention and treatment. The compositions containing the therapeutic targets and/or its relevant candidates and/or its derivatives or any other forms of the therapeutic target identified as the active ingredient can be administered in a wide variety of therapeutic dosage forms in conventional vehicles for administration. For example, therapeutic targets and/or its relevant candidates and/or its derivatives or any other forms of the therapeutic targets can be administered in such oral dosage forms as tablets, capsules (each including timed release and sustained release formulations), pills, powders, granules, elixirs, tinctures, solutions, suspensions, syrups and emulsions, nasal drops, an injectable, an infusion, or a form conjugated to a nanoparticle.

The pharmaceutical compositions can be provided to a biological organism by a variety of routes such as subcutaneous, topical with or without occlusion, oral, intramuscular, intravenously (both bolus and infusion), intraperitoneally, intramuscularly, subcutaneously, intracavity, or transdermally, inhalant, or other using forms well known to those of ordinary skill in the pharmaceutical arts.

A Formulation with Glycans, Lectins or Herbs and Small Molecules

Another subject of the present disclosure is a binding site-based drug formulation for the prevention or treatment of an infectious disease, a cancer, an autoimmune disease, an allergy, inflammation, a toxin-relevant biological injury or another disease in a target host. The drug formulation comprising at least one of the identified detection candidates or the identified target candidates, and derivatives thereof, The drug formulation consisted of at least one of the identified detection candidates or the identified target candidates, and derivatives thereof: 1) glycans including sialic acids and hydroxyl substituents thereof which has an identical or similar three dimensional structure to a glycan-related pathogen binding site or a glycan-related therapeutic target: to compete with the pathogen binding site or the therapeutic target; 2) lectins including but not limited to plant lectins or herbs or antibodies which can bind to a glycan-related pathogen binding site or a glycan-related therapeutic target: to block the pathogen binding site or the therapeutic target; and 3) small molecules including but not limited to sulfur containing compounds or products: to modify the chemical nature of the glycan-related pathogen binding site or the glycan-related therapeutic target.

Glycans, lectins, herbs, antibodies and small molecules are as described above.

Sulfur containing compounds or products include inorganic and organic compounds of sulfur. Inorganic compounds of sulfur include but not limited to sulfate ($SO_4^{2-}$), salts of sulfuric acid.

Organic compounds or products of sulfur include but not limited to a sulfonate, a sulfonyl, a sulurate, a sulfide, and a sulfur containing amino acid. The general formula of sulfonate is $RSO_2O^-$., where R is some organic group. They are conjugate bases of sulfonic acids with formula $RSO_2O$ H. As is common, the same term is used for compounds containing this functional group, ionic salts, or similar covalent compounds, esters. Sulfur containing compounds or products also include garlic products including but not limited to garlic powder, garlic oil and extract of garlic (Allicin, *Allium sativum*, Ajoene, etc.).

A sulfonyl group is an organic radical or functional group obtained from a sulfonic acid by the removal of the hydroxyl group. Sulfonyl groups can be written as having the general formula R—S($=$O)$_2$—R', where there are two double bonds between the sulfur and oxygen. The names of sulfonyl groups typically end in -syl, such as in tosyl chloride which is p-toluenesulfonyl chloride, $CH_3C_6H_4SO_2Cl$ or mesyl chloride which is methylsulfonyl chloride, $CH_3SO_2Cl$. Sulfonyl groups can be reduced to the hydrocarbon with lithium aluminium hydride ($LiAlH_4$).

An Anti-Infectious Pathogen Fabric or Surface

Another subject of the present disclosure is an anti-infectious pathogen fabric or anti-infectious pathogen surface will be created by the step of incorporating at least one of the identified detection candidates or the identified target candidates into or on fibers; or providing at least one of the identified detection candidates or the identified target candidates on supporting materials and making it into particles, and then attaching the particles onto a surface including but not limited to a cloth, a mask, a cap, or goggles.

Therapeutic Application of Sialic Acids

Sialic acid (Sia) is a generic term for the N- or O-substituted derivatives of neuraminic acid, a nine-carbon monosaccharide. Members of this group include: N-acetylneuraminic acid (Neu5Ac or NANA), 2-Keto-3-deoxynononic acid (Kdn), N-Acetylglucosamine (GlcNAc), N-Acetylgalactosamine (GalNAc), N-Acetylmannosamine (ManNAc), and N-Glycolylneur-aminic acid (Neu5Gc). The amino group bears either an acetyl or a glycolyl group. The hydroxyl substituents may vary considerably: acetyl, lactyl, methyl, sulfate and phosphate groups have been found. In addition, the small molecules in the present disclosure also include glycan binding molecules including but not limited to acetyl-, methyl- and sulfur-containing molecules as donors for acetylation, methylation and sulfatation of sialic acids or other glycans. Glycan-binding antibodies are also included. The products of sialic acids include substances containing at least one molecule of sialic acids and derivatives of sialic acids. Glycolipids (e.g. Ganglioside) are also included.

a. Blocking infection through competing with pathogen binding sites

In one embodiment of the invention, a sialic acid is used as an agonist drugs by competing with natural virus binding sites (or blocking) or toxins. The application of N-acetylneuraminicacid (Neu5Ac) for the prevention and treatment of viral infections of rotavirus, influenza A viruses H1N1, 2009 H1N1, H3N2 and H5N1, as well as allergy.

b. Modification of Sialic Acids

In one embodiment of the present invention, a sialic acid is modified using acetyl-, methyl- and sulfur-containing molecules as donors (drugs) for acetylation, methylation and sulfatation of sialic acids or other glycans. For example, methionine contains —S—$CH_3$ thus can be used as a donor to modify a pathogen binding site (a sialic acid or a glycan) into methylated and sulfated forms. Sulfur- and containing compounds such as sulfides (e.g. garlic products) as described in PCT/US2009/039810 can also act as donors of $CH_3$-S—S—$CH_3$. Such chemical modification of a sialic acid can attenuate even prevent pathogen binding to it.

The application of methionine, methionine-Zinc (Zn) complex and a formula consisted of Acetylneuraminic acid and methionine or methionine-Zn for the prevention and treatment of rotavirus infection; N-Acetylneuraminic acid, N-Acetylneuraminic acid methyl ester and a formula consisted of Acetylneuraminic acid methyl ester for the treatment of influenza infection are described in Exemplification (Table 4 and 5). The application of a garlic product for the prevention and treatment of viral infections of rotavirus, influenza A viruses H1N1, Newcastle disease viral (NDV), as well as allergy are described in PCT/US2009/039810. Such application of chemical molecules can be extended to other infections of other pathogens using sialic acids or other glycans as their binding sites.

c. Mis-Targeting of Microbial Sialidase

In another embodiment of the present invention, free sialic acids is used as false-targets, bind to and mis-activate (mis-lead) microbial or host sialidase. The mis-targeting protects host cells from being attacked by microbial sialidase, or protect the Sia-shedding on the surface of host cells. Further, microbial sialidase can be exhausted through inefficient work. This mechanism is different from the competitive inhibitors of sialidase. Metals can bind or conjugate to microbial sialidase and cell-surface (plasma membrane) and cytoplasmic sialidases, interrupt or inactivate sialidase function.

The application of N-acetylneuraminic acid (Neu5Ac) for the treatment of viral infections of rotavirus, influenza A viruses H1N1, 2009 H1N1, H3N2 and H5N1, as well as allergy are described in Exemplification.

d. Neutralizing Sialic Acid-Binding Molecules

In one embodiment of the invention, sialic acids or the derivatives of sialic acids are used to bind to and neutralize or modifying glycan-binding molecules of harmful toxins, lectins and antibodies and thus protect host cells.

Evidence supporting this mechanism of action is that after being treated (neutralization) with Neu5Ac, the harmful anti-rotavirus antibodies mentioned in the exemplification did not induce mouse deaths with rotavirus infection (Table 3).

Other supporting evidence is the efficacy of Neu5Ac and N-acetylneuraminic acid methyl ester for the treatment of the side effect of influenza antibodies. As described in exemplification, injection with moderate or high dose of antibodies against 2009H1N1 (swine), seasonal H1N1 and avian H5N1 influenza virus into day 15-16 or 18-19 chicken embryo induced either deaths or the leg disability of newborn chicks which is similar to the Guillain-Barre syndrome (GBS) in human (FIG. 14). However, newborn chicks with injection of the same antibodies pre-treated with N-acetylneuraminic acid (Neu5Ac) did not develop the syndrome.

New Vaccines and the Acting Mechanism of Antibody Therapy

In Vivo Proof of a Novel Action Mechanism of Vaccination and Antibodies

In vitro proof of a novel action mechanism of vaccination, passive immunity and antibody therapy has been described in PCT/US2007/018258. The functional mechanism is that antibodies induced by an infection or a vaccine or acquired through passive immunity bind to and block at least one binding site of a pathogen.

Figure 7:
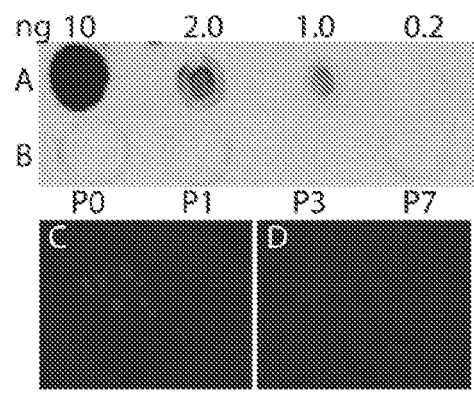
FIG. 7 is a graphical representation of detection of goat IgG in sera of pups delivered to those dams injected with goat anti-RV (B) by dot-blot hybridization. Various concentrations of goat IgG were used as controls (A). Binding of goat IgG to goblet cells of small intestine of the pups were detected at age of week 1 (C) by PE-anti-goat IgG, compared to a control without antibody treatment (D).

One example is that goat IgG in sera of pups delivered to those dams injected with goat-anti-rotavirus antibodies were undetectable at the day of birth. At the same time, binding of goat IgG to goblet cells of small intestine of the pups were detected at age of week 1 (FIG. 7) through week 3. In addition, oral administration of low dose of the same anti-rotavirus antibody showed efficacy for the prevention and treatment of rotavirus infection in a mouse model (PCT/US2007/018258).

Figure 8:
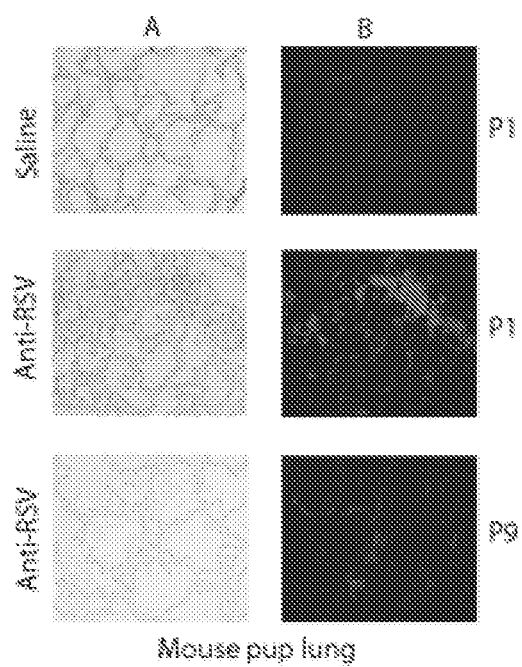
FIG. 8 is a graphical representation of in vivo binding of anti-respiratory syncytial virus (RSV) antibody to tissue sections of uninfected mouse pups.
Figure 9:
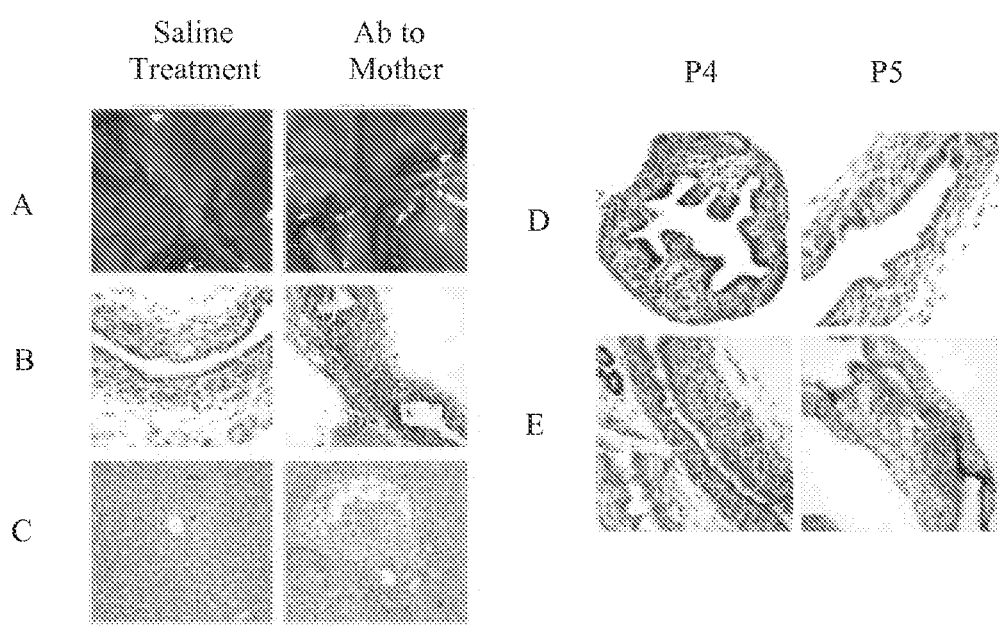
FIG. 9 is a graphical representation of histology changes induced by injection of goat anti-RV antibodies to pregnant mice. A-B: the bile duct and gall bladder of mouse pups at week 2 (A) and week 1 (B); C: mouse pup livers at week 1; D-E: the pup bile duct at P4 and P5.
Figure 10:
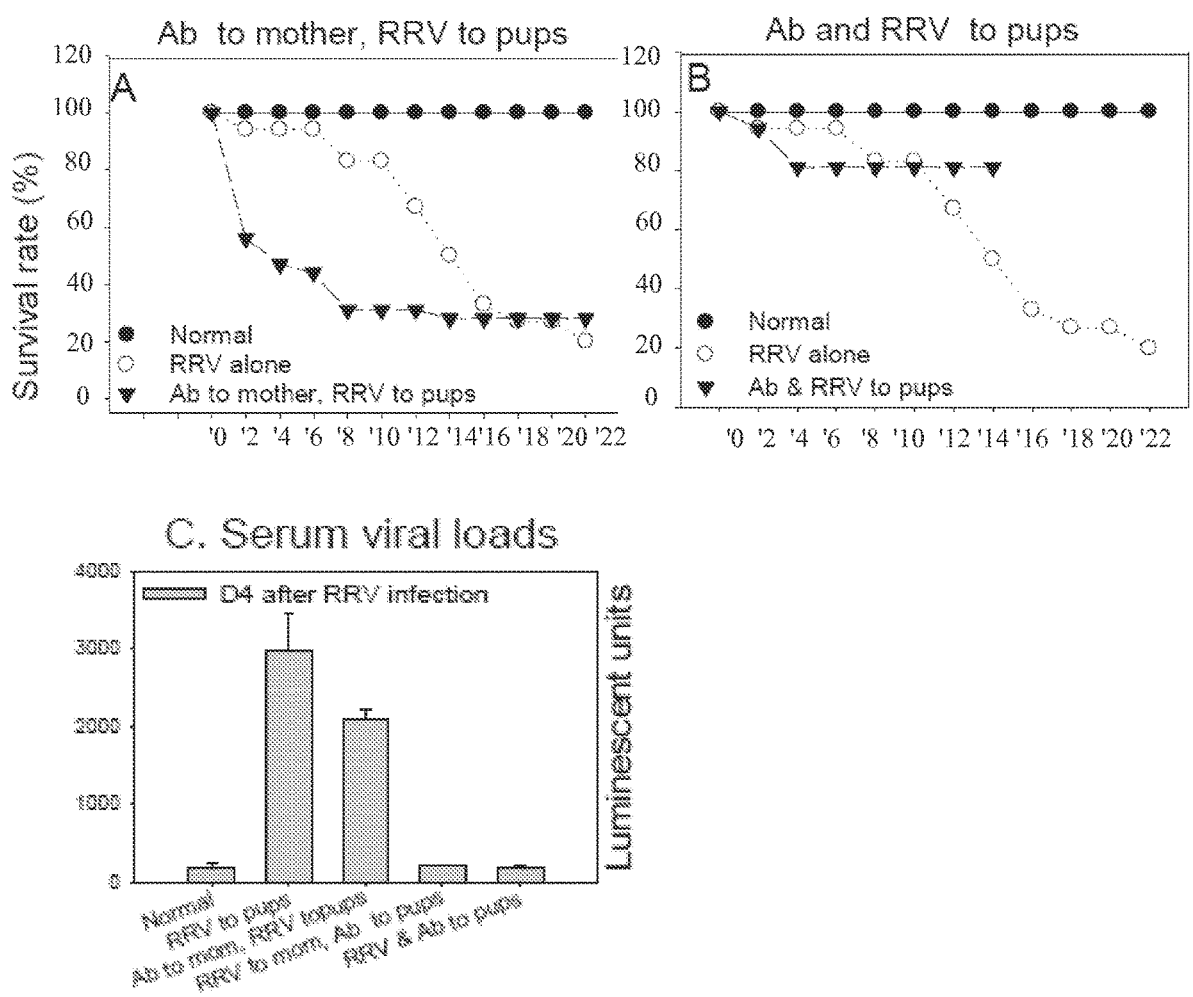
FIG. 10 is a graphical representation of survival curve of different mouse modules of rotavirus infection.

Similarly, binding of goat IgG to the lung of the mouse pups delivered to the dams injected with goat anti-respiratory syncytial virus (RSV) antibodies was detected up to age P9 (FIG. 8) and P14. Using anti-respiratory syncytial virus (RSV) antibodies such as Palivizumab (Synagis®) for protecting premature infants from severe RSV disease has shown efficacy. However, the mechanism of action of the drug is unclear. The mechanism of action disclosed in the present invention could be the functional mechanism of Palivizumab.

For further in vivo proof, day 16 (E16) chicken embryos were treated via allantois injection of anti-influenza virus immune sera; the blood were collected from the newborn chickens at day 3 after birth (day 8 after serum injection); then the chicks were infected with the 2009H1N1 (California) virus. The newborn chicks with injection of the sera containing anti-2009H1N1 (California) and seasonal H1N1 (Shanghai, 1999) viruses were not infected by the 2009H1N1 virus (Table 11). The antibody levels in the sera collected before viral infection were zero determined by an inhibitory hemagglutination test. Thus the action mechanism of the antibodies mentioned above was blocking of viral binding sites rather than neutralization of virus as described in exemplification.

Anti-pathogen antibodies as drugs for antibody prevention and therapy Anti-pathogen antibodies as drugs for antibody prevention and therapy have been described in PCT/US2007/018258. The present invention provides further in vivo proof As described above and in exemplification (Table 5, 6, 7, 10 and 11), low dose of following immune sera or antibodies can be used as drugs for antibody-prevention and antibody-therapy of influenza infections.

a. Anti-seasonal H1N1 virus antibodies for the prevention of the 2009H1N1 (swine), other H1N1 and H5N1 influenza virus infection;
 b. Anti-2009H1N1 (California) virus antibodies for the prevention of the 2009H1N1 (swine), other H1N1 and H5N1 influenza virus infection; and
 c. Anti-H5N1 virus antibodies for the prevention of the 2009H1N1 (swine), other H1N1 and H5N1 influenza virus infection.

Anti-Multiple Pathogen Vaccines for Influenza Infections

As described in exemplification, the anti-2009H1N1 (California) and anti-H5N1 immune sera (pre-treated with NeuSAc) were effective for prevention and treatment of the A/PR/8/34 (H1N1) virus infection in mouse pups (Table 5 and 6); the anti-H1N1 (seasonal) human sera and anti-H5N1 immune serum (pre-treated with NeuSAc) were effective for the prevention and treatment of the 2009H1N1 (California) virus infection in chicken embryos and newborn chicks (Tables 7 and 10). These results provide in vivo evidence that influenza viruses of 2009H1N1 (California), seasonal H1N1 and avian H5N1 share at least one binding site. Thus one embodiment of the present invention is disclosing following new vaccines based on the shared binding sites.

a. A seasonal H1N1 virus vaccine for the prevention of the 2009H1N1 (swine), other H1N1 and H5N1 influenza virus infection;
b. The 2009H1N1 (California) virus vaccine for the prevention of the 2009H1N1 (swine), other H1N1 and H5N1 influenza virus infection; and
c. A H5N1 virus vaccine for the prevention of the 2009H1N1 (swine), other H1N1 and H5N1 influenza virus infection.

Dualistic Roles of Antibodies

The roles of antibodies can be dualistic; they can act either as protectors by recognition and blocking pathogen binging sites; or disease inducers by triggering of certain harmful pathways as describe in PCT/US2007/018258. The present invention provides further in vivo proof.

a. High Levels of Antibodies are Harmful

As described in exemplification (Tables 5-10), high dose of the sera containing either anti-seasonal H1N1 antibodies or anti-2009H1N1 antibodies was not effective or harmful for the prevention of the A/PR/8/34 (H1N1) infection of newborn pups. Further, high dose of the sera induced either death or severe disease in chicken fetus and newborn chicks (Table 7 and FIG. 13).

b. Guillain-Barre Syndrome (GBS)

Injection with moderate or high dose of the anti-H1N1 and anti-H5N1 antibodies into E16 chicken embryo induced the leg disability of newborn chickens (FIGS. 13B, 13C, and 13D) which is similar to the Guillain-Barre syndrome (GBS) in human. The antibodies induced by the 2009H1N1 (California) virus is at highest risk for inducing GBS, followed by antibodies induced by the avian H5N1 (Anhui, 2005) virus and the seasonal-H1N1 (Shanghai, 1999) virus.

c. Pathogenic Mechanisms of Harmful Antibodies

Pathogenic mechanisms of harmful antibodies have been described in PCT/US2007/018258, PCT/US2009/039810 and U.S. 61/278,685. Other pathogenic mechanisms include but not limited to antibody-dependent cytotoxicity.

Treatment of Harmful Antibodies

One embodiment the present invention discloses using the following drugs and drug candidates for developing the treatment of a severe low respiratory infection including but not limited to 2009 H1N1, H5N1 and RSV infections, other infectious diseases, autoimmune diseases, cancers, obesity and other disorders to neutralize, dilute or interrupt the binding of harmful antibodies to their targets.

a. Sialic acids and derivatives including Ganglioside products;
b. Kinase inhibitors;
c. Beta-2 receptor inhibitors
d. Acetyl-, methyl- and sulfur-containing molecules as donors for acetylation, methylation and sulfatation of sialic acids or other glycans (modification and inactivation).
e. Immunoglobulin products or serum; and
f. Any other substances and approaches to interrupt kinase activating pathways or the binding of harmful antibodies to their targets.

Animal Models for Rapid Evaluation of Vaccines and Antibodies

One embodiment of the present invention is experimental models using cellular culturing or animals and anti-pathogen antibodies for evaluating efficacy and safety or side effect of vaccines or antibodies as described in exemplification. An experimental model for the pathogenesis study of Guillain-Barre syndrome (GBS) and evaluation of side effect of influenza vaccines and antibodies is also described in exemplification (FIG. 12 and FIG. 13). These experimental models can be used but not limited for screening drugs for prevention and treatment of GBS or for the rapid evaluation of the efficacy and safety of vaccines and antibodies.

Examples

1. An Array Carrier

FIG. 1 shows an example of an array chip. A, B, C, D, E and F represent different kinds of target candidates attached to the chip; G represents an example of histochemistry staining; and H represents an example of fluorescent staining.

2. Primary Screening of Potential Therapeutic Targets Using Plant Lectins

FIG. 2 and FIG. 3 show examples of screening of potential biological therapeutic targets using plant lectins as detection candidates. Plant lectins used were purchased from Vector Laboratories (California, USA) and included: wheat germ agglutinin (WGA) which specifically recognizes N-Acetyl-D-Glucosamine, *Ulex Europaeus* agglutinin I (UEA I) which specifically recognizes α-Focus, and soybean agglutinin (SBA) which specifically recognizes N-Acetyl-D-Galactosamine. All lectins were labeled with biotin, and another kind of WGA was labeled with a fluorescent (Rhodamine). The secondary reagent for biotin-labeled lectins was fluorescent (Texas Red) conjugated-streptavidin.

Biotin-labeled lectins WGA and SBA were incubated for one hour separately with tissue sections of heart, lung, liver, kidney and spleen of a bulb/c adult mouse (FIG. 2); WGA and UEA I were incubated separately with tissue sections of small intestines of bulb/c newborn pups and adult mouse (FIG. 3); and WGA were incubated separately with tissue sections of liver and small intestine of bulb/c mouse pups infected or uninfected with rhesus rotavirus (RRV) (FIG. 4). After wash, streptavidin-Texas Red was added and incubated for 30 minutes followed by wash and detection with a fluorescent microscope. Positive binding is shown as areas stained brightly (white) and negative binding as areas not stained brightly (grey areas).

As shown in FIG. 2 and indicated by binding of WGA, N-Acetyl-D-Glucosamine is expressed strongly on part but not all of heart, lung; moderately on certain cells of spleen; and negatively on liver and kidney of bulb/c mice (FIG. 2A). Indicated by binding of SBA, NAcetyl-D-Galactosamine is expressed moderately on certain cells of spleen and negatively on heart, lung, liver and kidney of bulb/c mice (FIG. 2B). As shown in FIG. 3 and indicated by binding of WGA and EUA I, N-Acetyl-D-Glucosamine (FIG. 3A) but not α-Focus (FIG. 3B) is expressed stronger on small intestine of day 2 and day 4 newborn mouse pups and weaker on small intestine of adult mice. Based on the primary screening results, N-Acetyl-D-Glucosamine and N-Acetyl-D-Galactosamine are potential biological markers related to diseases. Whether they are binding sites of a pathogen will be detected by binding of the pathogen and WGA or SBA to an array chips consisted of healthy tissue sections of humans, animals, and plants or various cell lines as illustrated above.

This process will be easily extended to bind other lectins specific for other glycans to the array chip mentioned above to detect other glycan-related potential biological markers existing in humans, animals and other organisms.

3. Identification of Glycan-Related Biological Markers

Figure 4:
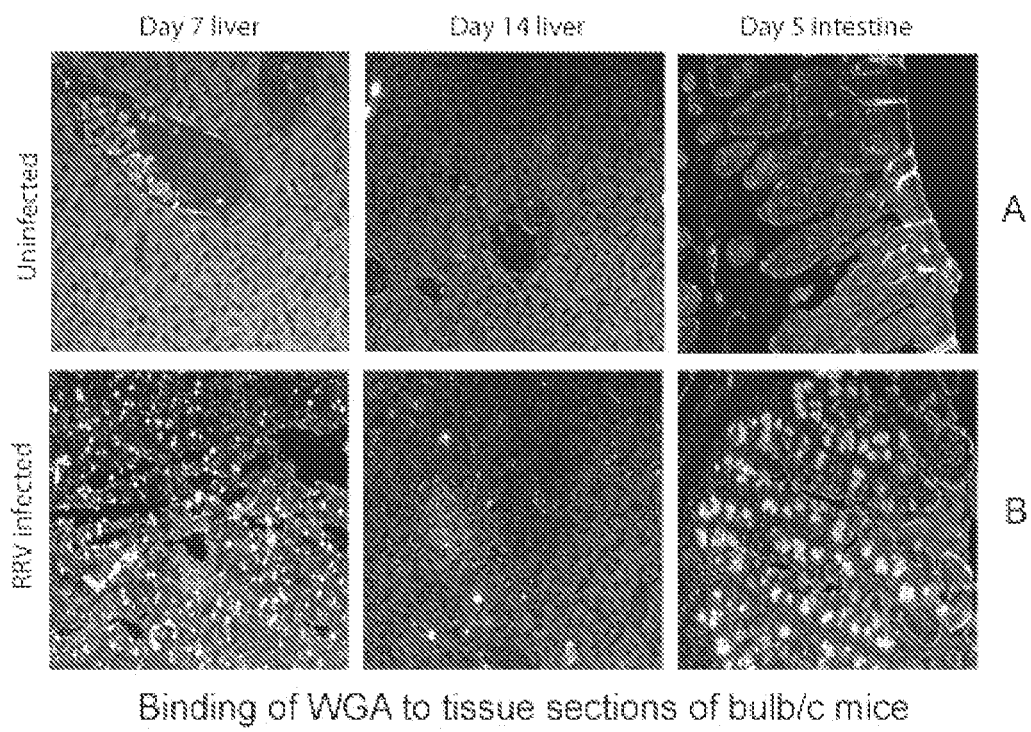
FIG. 4 is a graphical representation of binding of plant lectin WGA to tissue sections of rhesus rotavirus (RRV) infected and uninfected mouse pups.

FIG. 4 shows an example of identification of a glycan-related biological marker by binding of WGA to healthy and disease tissue sections.

Two groups of sucking bulb/c mouse pups were treated at day 2 after birth via oral administration with 30 μl of saline (uninfected group) and 30 μl of RRV at concentration of $1\times10^7$ pfu/ml (RRV infected group). The course of this viral illness is that within week 1 after RRV infection, the pups have diarrhea with alcoholic stools, don't eat well and fail to gain weight as quickly as healthy mice; and 30-40% of pups with serious illness become jaundiced. By the 2nd week all the mice become jaundiced, don't eat well and fail to gain weight; and 80% of pups with serious illness died. Viruses are usually cleared within 5 days and undetectable at day 5. Pups were sacrificed at different days after treatment and samples of sera, snap-frozen and formalin-fixed tissues of intestine and liver, were processed.

As shown in FIG. 4 and indicated by binding of WGA, the livers and small intestines from mouse pups infected with RRV within one week (acute phase) were filtrated with inflammatory or proliferating cells with strong expression of N-Acetyl-D-Glucosamine (FIG. 4B). The livers and small intestines from healthy pups without RRV infection are negative for the glycan expression (FIG. 4A). Therefore, glycan N-Acetyl-D-Glucosamine is a potential biological marker related to inflammation.

In another experiment, WGA binding to human healthy and disease tissues was detected with a tissue array chip consisted of FDA normal human organs (Array I+II)+bonus malignant samples (Immgenex, San Diego, USA). The results showed that majority of normal human organs except bone marrow, salivary gland and hypophysis do not or weakly express N-Acetyl-D-Glucosamine, while following cancer tissues strongly express N-Acetyl-D-Glucosamine: malignant melanoma, brain malignant oligodendroglioma, kidney clear cell carcinoma, skin basal cell carcinoma of head, throat carcinoma, Hodgkin's lymphoma of supraclavicular, colon intermediate grade interstitialoma, thyoid medullary carcinoma and skin squamous cell carcinoma of left chest wall.

Similarly, other biological markers relating to cancers and other diseases can be easily identified by binding of WGA and other lectins specific for other glycans to an array chip consisted of healthy and cancer tissue or other disease tissue sections of humans and animals, or various tumor cell lines as illustrated above.

4. Identification of Potential Disease Inducers

Figure 5:
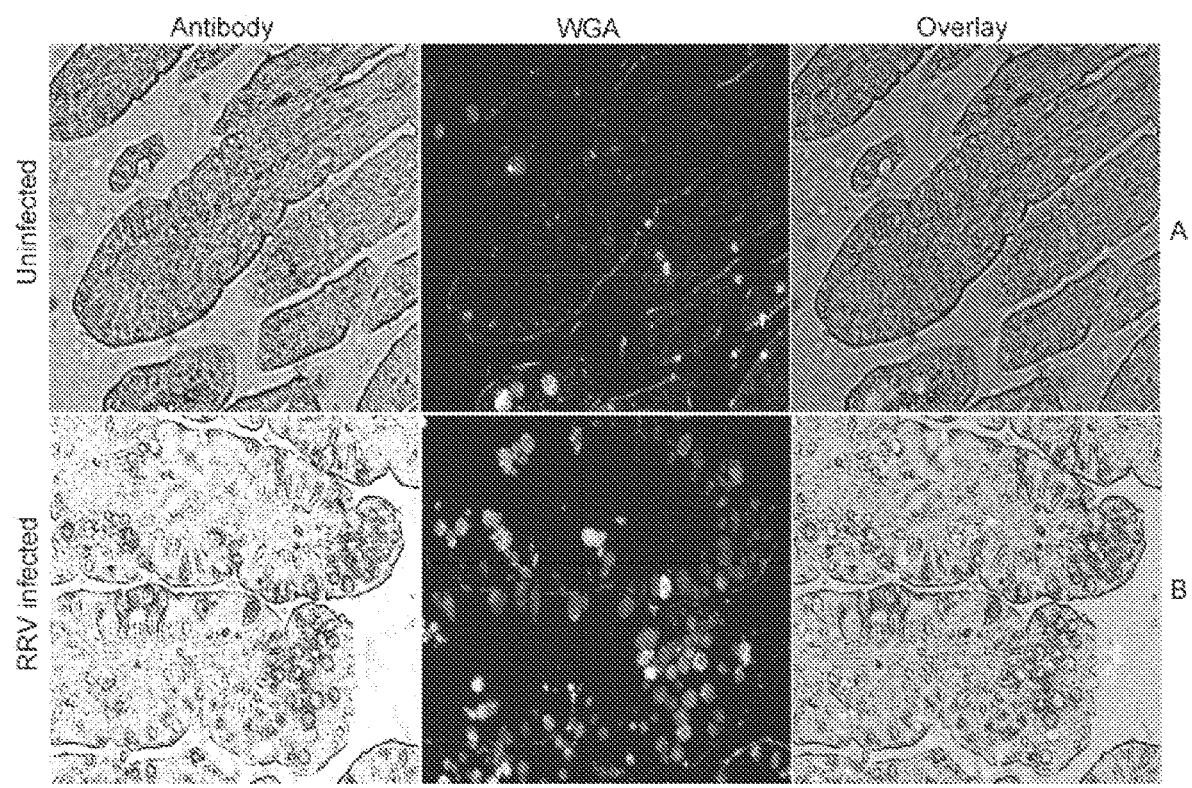
FIG. 5 is a graphical representation of binding of an anti-RRV polyclonal antibody and lectin WGA to tissue sections of RRV infected and uninfected mouse pups.

FIG. 5 shows an example of identification of potential disease inducers by binding of an anti-rotavirus (RV) polyclonal antibody and lectin WGA to tissue sections of RRV infected and uninfected mouse pups. The biotin-labeled anti-RV polyclonal antibody was purchased from Meridian Life Science, Inc (Mine, USA). Briefly, the Rhodamine-labeled WGA and the biotin-labeled anti-RV antibody were incubated for one hour with tissue sections of small intestines from the uninfected and infected mouse pups as mentioned above. After wash, streptavidin-conjugated horseradish peroxidase (HRP) was added and incubated for 30 minutes followed by wash, HRP substrate DAB was added and incubated for 15 minutes followed by was and detection with a regular and fluorescent microscope. Positive binding for the antibody is shown as areas stained brown, and positive binding for WGA is shown as areas stained brightly red and negative binding as areas not stained brightly (dark areas).

As shown in FIG. 5, the anti-RV antibody binds to the same proliferating goblet cells expressing N-Acetyl-D-Glucosamine (FIG. 5B) in the small intestine of RRV infected pups (day 5 after RRV infection). In an acute viral infection, viruses are usually cleared within one week, and anti-virus antibodies are at elevated levels from week 1 and reach peak levels at week 2 to week 3. Because anti-RV antibodies bind to proliferating cell expressing N-Acetyl-D-Glucosamine, these antibodies can cause inflammation even after viral clearance. This inflammation in turn leads to a proliferative response of the host defense system, which further exposes the glycan target. Thus, anti-RV antibodies can be an inflammatory inducer and a cause of autoimmune diseases of tissues or organs expressing N-Acetyl-D-Glucosamine. If the proliferating inflammation persists long an autoimmune diseases can be developed. If the proliferating inflammation eventually leads to an uncontrollable cell growth, a cancer can be developed. For these reasons, anti-RV antibodies can be an inducer of autoimmune diseases and cancers. This will be further detected by comparison of binding of anti-RV antibodies and WGA to healthy and disease tissues sections attached on an array chip.

Similarly, other potential disease inducers can be easily identified by binding of other antibodies against other pathogens and WGA or other lectins specific for other glycans to an array carrier consisted of disease tissue sections of humans and animals, or various tumor cell lines as illustrated above.

5. A Drug Formulation for Prevention and Treatment of Viral Infections and Allergy A drug formulation consisted of commercially available synthetic N-Acetylneuraminic acid (Neu5Ac) (JunKang Biotech Co., Ltd, Guangzhou, China) and garlic oil products (Nature's Bounty, INC, New York, USA) was tested for its efficacy on prevention and treatment of viral infections and allergy as described below.

5.1. Prevention of Rotavirus Viral Infection

Figure 6:
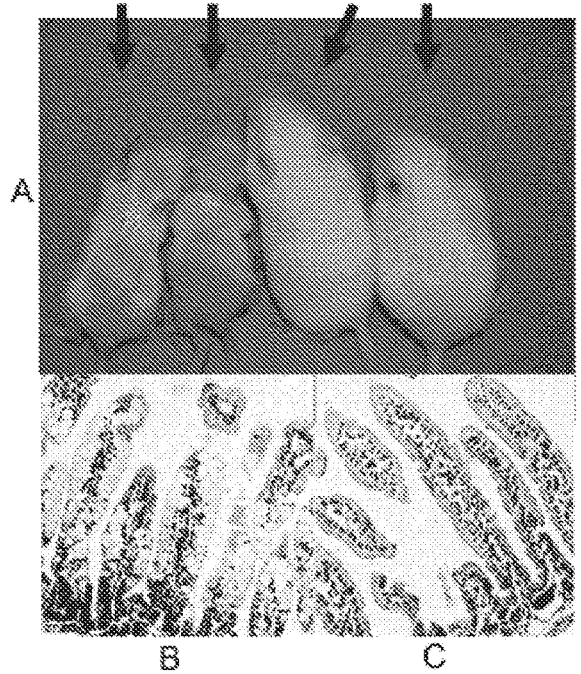
FIG. 6 is a graphical representation of RRV infected mouse pups treated with a formulation and saline.

Three groups of sucking bulb/c mouse pups were treated at day 1 after birth via oral administration with 1) 20 μl of saline (saline treated control group, n=21); 2) 20 μl of the garlic oil at the concentration of 1-5 μg/g body weight; and 3) 20 μl of the formulation consisted of the Neu5Ac (0.5-2 μg/g body weight) and the garlic oil (1-5 μg/g) (drug treated group, n=20), followed by challenging with RRV at day 2 as described above. Mice were kept for 3 weeks after RRV infection. Pups pretreated with the garlic oil product alone or the formulation consisted of the Neu5Ac and the garlic oil product were not infected compared to control pups pretreated with saline. Representative 2 week-old pups pretreated with saline and the formulation are shown in FIG. 6A, and the representative histology changes of small intestine of day 4 pups are shown in FIG. 6B (saline pretreated) and 6C (formula or drug pretreated). The results with statistical analysis are concluded in Table 2.

TABLE 2

The results of efficacy test of a formulation consisted of Neu5Ac and garlic oil

| Test Subject | Pathogen or Disease | Saline *Effec | Saline Ineffec (%) | Formulation Effec | Formulation Ineffec (%) | Odd Ratio (OR) | 95% CI | P value |
|---|---|---|---|---|---|---|---|---|
| Bulb/c mice | RRV | 4 | 17 (81) | 18 | 2 (10) | 0.03 | 0.03~0.47 | <0.0001 |
| Chicken | NDC | 1 | 9 (90) | 7 | 3 (30) | 0.05 | 0.13~0.88 | 0.02 |
| Chicken embroy | H1N1 | 1** | 10 (91) | 9 | 1 (10) | 0.01 | 0.02~0.71 | 0.0003 |
| Human | Flu | 1 | 14 (93) | 15 | 1 (6.3) | 0.005 | 0.01~0.45 | <0.0001 |
| Human | Allergy | 2 | 13 (87) | 14 | 1 (6.7) | 0.07 | 0.01~0.52 | <0.0001 |

*Effec = effective, Ineffec = ineffective;
**Viral titer lower than 1:16 were counted as effective.

5.2. Prevention and Treatment of Newcastle Disease Viral (NDV) Infection

Two groups of SPF chickens (4 weeks, ~2 kg) were pretreated via nasal drop and oral administration with 2 ml of saline (saline treated control group, n=10), or 2 ml of the formulation at the concentration of 1 mg/ml of each NeuSAc and the garlic oil (drug treated group, n=10), followed by challenging with highly pathogenic NDV next day. 20 ml of saline or the formulation were separately added to 200 ml of drinking water of each group once at day 3 after viral infection. The course of this viral illness is that within one week after NDV infection, the chickens have diarrhea, don't eat well, and more than 50% of chickens die. The chickens were kept for 8 days after NDV infection.

At day 8 after NDV infection, 7/10 (70%) of chickens treated with saline were died and another 2 chickens were sick with diarrhea and did not eat; 1/10 (10%) of chickens treated with the formulation was died and another 2 were sick. The formulation reduced total death rate of the NDV infection from 70% to 10% (Odd Ratio=0.05, 95% CI=0.02-0.96, P=0.02). As concluded in Table 2, the formulation reduced total sick (death+sick=ineffective) rate of the NDV infection from 90% to 30%.

5.3. Prevention and treatment of influenza viral infection of chicken embryos Two groups of chicken embryos were pretreated via injection with 100 µl of saline (saline treated control group, n=12), or 100 µl of the formulation as mentioned above at the 20 concentration of 0.5 mg/ml of each NeuSAc and the garlic oil (drug treated group, n=12), followed by inoculation of influenza viral stain H1N1 into the allantois next day. 100 µl of saline or the formulation were separately injected into the allantois once everyday after viral inoculation and allantois fluid was collected at 48 hours after viral inoculation and viral titers in the fluid were determined by a hemagglutination test.

The viral titers of 10/12 of chicken embryos treated with saline were 1:256, and the viral titers of 9/12 of chicken eggs treated with saline were below 1:16 that were counted as effective in Table 2. The chicken embryos with viral titer of zero in their allantois fluid (1 for saline treatment and 2 for formula treatment) were not included in statistical analysis in order to exclude the possible failure of viral inoculation. As concluded in Table 2, the formulation significantly inhibited H1N1 infection of chicken embryos.

5.4. Treatment of Influenza of Humans

Two groups of human subjects with influenza were treated twice every day for 2-3 days via nasal drop and oral administration each time with 15 ml of saline (saline treated control group, n=15), or 15 ml of the formulation at the concentration of 1 mg/ml of each Neu5Ac and the garlic oil product (drug treated group, n=16). Symptoms of influenza include fever, headache, tiredness, cough, sore throat, runny or stuffy nose, body aches, or diarrhea. The illness course is usually one week. The subjects were observed everyday for symptoms of influenza for 7 days. Compared to the subjects treated with saline, 15 subjects treated with the formulation had significantly reduced symptoms and shorter illness course (5-7 days versus 3-4 days). Those subjects were counted effective in Table 2.

5.5. Treatment of Allergy of Humans

Two groups of human subjects with seasonal allergy were treated every day for 2-3 days via nasal drop each time with 1-2 ml of saline (saline treated control group, n=15), or 1-2 ml of the formulation at the concentration of 1 mg/ml of each NeuSAc and the garlic oil (drug treated group, n=15). Symptoms of allergy include nasal congestion, runny nose, sneezing and itchy nose. The subjects were observed everyday for symptoms of allergy for 3 days. Compared to the subjects treated with saline, 14 subjects treated with the formulation had significantly reduced allergic symptoms. Those subjects were counted effective in Table 2.

Drug Candidates for Prevention and Treatment of Viral Infections

The following drug candidates were tested for its efficacy on prevention and treatment of viral infections and allergy as described below.

a. Synthetic N-Acetylneuraminic acid (NeuSAc) (JunKang Biotech Co., Ltd, Guangzhou, China).
   Formula: $C_{11}H_{19}NO_9$
   Molecular weight: 309.3.
   Purity (HPLC): 98.7%.

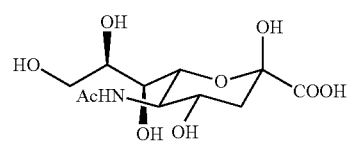 [SMILES: CC(=O)NC1C(O)CC(O)(C(=O)O)OC1[C@@H](O)[C@H](O)CO]

b. Methionine (J.R. Carlson Laboratories, Inc., Arlington Hts, Ill., USA).
   Formula: $C5H11NO_3S$
   Molecular weight: 149.21

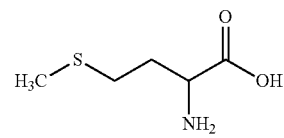

c. A garlic oil product contains 10 mg of *allium sativum* per softgel (Nature's Bounty, INC, New York, USA). The effective component is mainly diallyl disulfide.

Formula: $C_6H_{10}S_2$
Molecular weight: 146.28

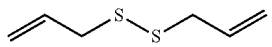

d. A purified goat polyclonal antibody against the bovine rotavirus strain NCDV (Nebraska Calf Diarrhea Virus) (Meridian Life Science, Inc., Saco, Me., USA).
Purity: >95%
Concentration: 5 mg/ml.
e. A monoclonal antibody reacts with P41 major capsid protein (VP6) of bovine and human rotavirus isolates (Meridian Life Science, Inc., Saco, Me., USA).
Purity: >95%
Concentration: 0.1 mg/ml.
f. Diethyl disulfide (Lida Chemicals, Shijiazhuang, China).
Formula: $C_4H_{10}S_2$
Structure: $CH_3CH_2SSH_2CH_3$
g. Methionine-Zinc (Zn) complex (Jiande Biotech, Zhejiang, China)
Zinc (Zn): 25%.
h. Synthetic N-Acetylneuraminic acid methyl ester (JunKang Biotech Co., Ltd, Guangzhou, China).
Molecular weight: 323.3
Formula: $C_{12}H_{21}NO_9$
Structure: See right

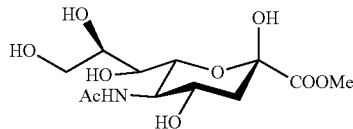

5.7. Prevention and Treatment of Rotavirus Viral Infection with Formulations

Four groups of sucking bulb/c mouse pups were treated at day 1 after birth (P1) via oral administration with saline (control group) or drug candidate followed by challenging at day 2 (P2) with 20 μl (microliter) of rhesus rotavirus (RRV) at the concentration of $1\times10^7$ PFU/ml. The different groups of mice were treated with each 20 μl (microliter) of: 1) saline (RRV group, n=11); 2) NeuSAc at the concentration of 2 mg/ml (Sia group, n=13); 3) methionine at the concentration of 2 mg/ml (Met group, n=12); and 4) a formulation consisted of the NeuSAc (2 mg/ml) and the methionine (2 mg/ml) (formula-1, n=12). Mice were kept for 3 weeks after RRV infection.

TABLE 3

The results of efficacy test of drug candidates for rotavirus (RRV) infection

| Drug candidate | Sick | Not sick | Sick Rate(%) | Odds Ratio | 95% CI | P value |
|---|---|---|---|---|---|---|
| Saline | 9 | 2 | 81.8 | 4.5 | 0.10-0.79 | 0.01 |
| Neu5Ac | 3 | 10 | 23.1 | 0.07 | 0.01-0.49 | 0.01 |
| Methionine | 3 | 9 | 25.0 | 0.07 | 0.01-0.56 | 0.01 |
| Neu5Ac + Meth* | 2 | 10 | 16.7 | 0.01 | 0.01-0.38 | 0.003 |

*Meth = Methionine.

The course of rotavirus infection is that within week 1 after RRV infection, the pups have diarrhea with alcoholic stools, don't eat well and fail to gain weight as quickly as healthy mice; and some pups with serious illness become jaundiced. By the 2nd week all the mice become jaundiced, don't eat well and fail to gain weight; and 80% of pups with serious illness died. Viruses are usually cleared and undetectable within one week.

Pups pretreated with the drug candidates were not infected compared to control pups pretreated with saline. The results with statistical analysis are concluded in Table 3. The effective dosages of drug candidates for rotavirus infection for human are calculated and listed in Table 4.

TABLE 4

The dosages of drug candidates for rotavirus infection

| Drug candidate | Low (mg/kg) | High (mg/kg) | Range (mg/kg) |
|---|---|---|---|
| Neu5Ac | 0.1 | 20 | 0.1-20 |
| Metnionine | 0.1 | 20 | 0.1-20 |
| Neu5Ac + Meth* | 0.1:0.1 | 20:20 | 0.1:0.1-20:20 |

5.8. Prevention and Treatment of Rotavirus Infection with Low Dosage of Antibodies Five groups of bulb/c pups were treated at P0 via oral administration with each 20 μl (microliter) of saline solution containing different drug candidates followed by oral inoculation of 20 μl (microliter) of RRV ($1\times10^7$ PFU/ml) at P1. The different treatments include: 1) saline alone (RRV alone, n=11); 2) the anti-NCDV antibodies (10 μg) (Ab-1+RRV, n=15); 3) the anti-VP6 monoclonal antibody (1 μg) (Ab-2+RRV, n=12); 4) a combination of the anti-NCDV (10 μg) and the anti-VP6 (1 μg) antibodies (Ab-1 & Ab-2+RRV, n=8); and 5) a formulation consisted of the anti-NCDV antibodies (50 μg) and the Neu5Ac (25 μg) (formula-2, n=6). Mice were kept for 3 weeks after RRV infection.

TABLE 5

The results of efficacy test of antibody therapy for rotavirus infection

| Drug candidate | Sick | Not sick | Sick Rate(%) | Odds Ratio | 95% CI | P value |
|---|---|---|---|---|---|---|
| Saline | 9 | 2 | 81.8 | 4.5 | 0.10-0.79 | 0.01 |
| Ab-1* | 5 | 10 | 33.3 | 0.11 | 0.02-0.72 | 0.02 |
| Ab-2** | 2 | 10 | 16.7 | 0.04 | 0.005-0.38 | 0.003 |
| Ab-1 + Ab-2 | 1 | 7 | 12.5 | 0.03 | 0.002-0.43 | 0.005 |
| Ab-1 + Neu5Ac | 1 | 5 | 16.7 | 0.04 | 0.003-0.62 | 0.02 |

*anti-NCDV antibody;
**anti-RV-VP6 antibody.

The course of rotavirus infection is as described above. The results with statistical analysis are concluded in Table 5.

In combination with the results of PCT/US2007/018258, the efficacy data showed that 1) low dosage of the anti-NCDV antibodies (less than 20 μg/each pup) reduced the severity and shorten the course of rotavirus infection; 2) the anti-VP6 antibody alone or in combination with the anti-NCDV antibodies prevented rotavirus infection; and 3) Neu5Ac reduced the toxicity (see below) of the anti-NCDV antibodies.

5.9. Prevention and Treatment of Influenza Infection of Chicken Embryos

Four groups of chicken embryos were pretreated via injection with 100 μl of saline solution containing 1) saline alone (control group, n=10); 2) 50 μg of the Neu5Ac (Neu5Ac group, n=10); 3) 40 μg of the *allium sativum* (garlic group, n=5); and 4) 40 μg of the Neu5Ac and 40 μg of the *allium sativum* (formula-2 group, n=5), followed by inoculation of the 2009 H1N1 (swine) influenza viral stain (California) into the allantois next day. Another two groups of chicken embryos with the same treatment with saline (control) and 50 μg of the Neu5Ac were inoculated with seasonal H1N1 (China) virus. 100 μl of saline or the Neu5Ac solution were separately injected into the allantois once everyday after viral inoculation and allantois fluid was collected at 48 hours after viral inoculation and viral titers in the fluid were determined by a hemagglutination test.

The viral titers of 3/5 of chicken eggs treated with the garlic were 1:16 or 1:32; and the viral titers of 3/5 of chicken eggs treated with the formula-2 (Neu5Ac+garlic) were 1:1 or 1:2. The results are summarized below.

| | Group | | |
|---|---|---|---|
| | 1 | 3 | 4 |
| Treatment | Saline | Garlic | Formula-2 |
| Viral titer | 1:256 | 1:16-32 | 1:1-2 |

5.10. Treatment of Side Effect of Avian (H5N1) Influenza Vaccine with NeuSAc

SPF chickens (4 weeks, ~2 kg) were sick after 3 weeks of the treatment with a H5N1 vaccine candidate. Sick chickens looked tired and did not eat well. Two groups of the sick chickens were treated once a day via oral administration with 2 ml of saline (control group, n=7), or 2 ml of the NeuSAc at the concentration of 2 mg/ml (drug treated group, n=8), for three days. At the first day of treatment, chickens with NeuSAc treatment looked and ate better. At day 3, 7/8 of the sick chickens recovered and looked normal while 6/7 of the saline-treated control group still sick. The NeuSAc reduced the side effect of the H5N1 vaccine candidate from 87.5% to 12.5% (Odd Ratio=0.02, 95% CI=0.001-0.40, P=0.01).

6. Pathogenic Antibodies

Antibodies can be harmful if they bind to a molecule linking to a harmful activating pathway such as kinase pathways.

6.1. Antibodies from Pregnant Mother Induced Disease

Pregnant bulb/c mouse dams were treated via intraperitoneal injection with 250 μg of the anti-NCDV antibodies three times at E14, E16 and E18 before delivery without RRV inoculation to pups (n=21). 7 (33.3%) of the pups delivered to those dams were died at birth; and 52.4% of the pups failed to gain weight from day 10 after birth, and developed an illness that was similar to experimental biliary atresia (obstruction of bile duct). The bile duct and gall bladder of the pups looked twisted at week 2 when compared to the bile duct and gall bladder of control pups delivered to the dams treated with saline (FIG. 9A). Further, significant proliferation of bile duct epithelium cells (FIG. 9B) and infiltration by inflammatory cells in liver (FIG. 9C) was observed at week 1 in those pups (FIG. 10: Ab to mother). In another experiment, injection of 15 μg of anti-RV antibody once at E18 caused significant inflammatory proliferation of bile duct epithelium cells at P4 and those proliferating cells blocked the bile duct from P5 (FIG. 9E) compared to normal control pups (FIG. 9D).

6.2. Antibodies Plus RRV Induced Severe Viral Infection

Four groups of bulb/c pups were treated via intraperitoneal injection with each 20 μl (microliter) of 1) saline at P0 and RRV at P1 (control group, n=21); 2) the anti-NCDV antibodies (50 μg) at P0 and RRV at P1 (Ab+RRV, n=14); 3) RRV at P0 and antibodies (50 μg) at P1 (RRV+Ab, n=10); 4) Antibodies (75 μg) to pregnant mouse at pregnant day 18 (E18) and RRV to pups at P0 (Ab to mom+Ab, n=21); and 5) 250 μg of the anti-NCDV antibodies three times at E14, E16 and E18 before delivery without RRV inoculation to pups as mentioned above. The RRV concentration was $1\times10^7$ PFU/ml. Mice were kept for 3 weeks after RRV infection.

TABLE 6

The results of high dose of antibodies in rotavirus infection

| Treatment | Pup number | Death | Sick | Death (%) | Sick (%) |
|---|---|---|---|---|---|
| Saline + RRV | 28 | 9 | 24 | 32.1 | 85.7 |
| *Ab (pup) + RRV | 14 | 4 | 11 | 28.6 | 78.6 |
| RRV + Ab (pup) | 10 | 1 | 6 | 10.0 | 60.0 |
| Ab (mom) + RRV | 21 | 10 | 20 | 47.6 | 47.6 |
| Ab to mom | 21 | 7 | 11 | 33.3 | 52.4 |

*Ab = anti-NCDV antibody

The course of rotavirus infection is as described above. The results are summarized in Table 6 and FIG. 10.

As shown in FIG. 10, the pups delivered to those dams with antibody treatment before delivery (FIG. 10A) developed the disease earlier and more severely as compared to pups treated with RRV alone (FIG. 10A).

6.3. Antibodies can Induce Cancers

The following tissue sections of pup bile ducts were detected for binding of anti-NCDV antibody and proliferation (inflammation) cells using FITC-conjugated anti-goat IgG antibody, Texas-Red-conjugated anti-proliferating cell nuclear antigen (PCNA) and immunofluorescent staining.

1) Saline to mother without RRV infection (Normal);
2) RRV to pups (RRV);
3) Anti-NCDV to mother without RRV infection (Ab);
4) Anti-NCDV to mother and RRV to pups (Ab+RRV).

Goat IgG bound to the proliferating bile duct epithelium cells (FIG. 11: HE stain) were detected on the bile duct of the pups with the treatment of antibody to mother with and without RRV to pups as mentioned above (FIG. 11: Ab and Ab+RRV of the raw of NCDV). These positive results were compared to the immunofluorescent staining of the bile duct of the pup groups of saline and RRV as negative controls for anti-NCDV-binding (FIG. 11: Saline and RRV of the raw of NCDV).

Further, a marker for proliferation, proliferating cell nuclear antigen (PCNA) was detectable on the proliferating cells of the two groups with anti-NCDV treatment especially the pups with antibody to mother without RRV infection, compared to the other two groups (FIG. 11: raw of PCNA). The anti-NCDV antibody also bound to the liver section of a P2 pups treated with antibody to mother compared to the pups treated with saline. The raw of overlay showed that the anti-NCDV antibodies bound to the same cells expressing PCNA.

Aberrant expression of PCNA has been reported in various malignancies. Because the anti-NCDV antibodies stimulated inflammatory cells expressing PCNA and many cancers are initiated from inflammation, the antibodies induced during a infection have the potential to induce cancers. This can occur if such antibody stimulation exists persistently and eventually leads to an uncontrolled cell growth.

As described in PCT/US2009/039810, the anti-NCDV antibodies bound to N-Acetyl-D-Glucosamine. Therefore, glycan N-Acetyl-D-Glucosamine is a potential biological marker related to inflammation and cancers.

7. Diagnosis Kits for Rotavirus Infection A sandwich ELISA kit for detection of rotavirus was developed as below.
- a. Capture antibody: the monoclonal anti-VP6 antibody (0.1 mg/ml) (Meridian Life Science, Inc., Saco, Me., USA): 1:200 dilution.
- b. Detection antibody (primary): the purified goat polyclonal anti-NCDV antibody (5 mg/ml) (Meridian Life Science, Inc., Saco, Me., USA): 1:200 dilution.
- c. Secondary detection antibody: an anti-goat IgG antibody (Meridian Life Science, Inc., Saco, Me., USA).

Figure 12:
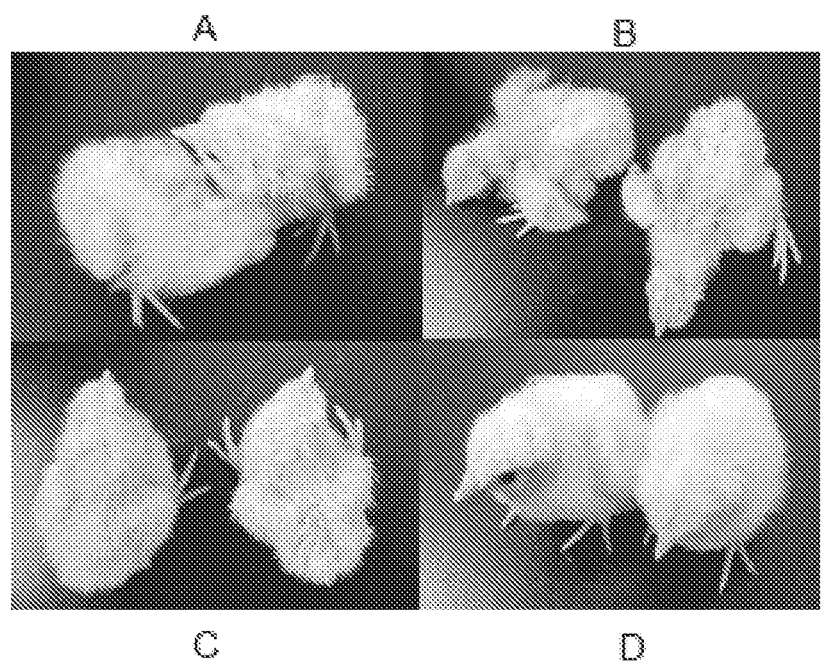
FIG. 12 is a graphical representation of 2009 H1N1 influenza virus-infected newborn chicks. Chicken embryo were pre-treated at E16 with saline (A), anti-2009H1N1 (California) virus serum (B), anti-seasonal H1N1 (Shanghai, 1999) virus serum (C), and a formula consisted of the anti-2009H1N1 (California) serum and Neu5Ac (D), followed by viral inoculation at E17.

Viral loads in the sera from mouse pups infected with RRV were detected by the ELISA kit and the results are shown in FIG. 12C.

8. Other Drug Candidates for Prevention and Treatment of Viral Infections 8.1. Prevention and Treatment of Rotavirus Viral Infection Three groups of sucking bulb/c mouse pups were treated at day 1 after birth (P1) via oral administration with saline (control group) or drug candidate followed by challenging at day 2 (P2) with 20 µl (microliter) of rhesus rotavirus (RRV) at the concentration of $1 \times 10^7$ PFU/ml. The different groups of mice were pre-treated with each 20 µl (microliter) of: 1) saline (RRV group, n=7); 2) the methionine-Zinc (Zn) complex at the concentration of 2 mg/ml (Met group, n=7); and 3) a formulation consisted of the Neu5Ac (2 mg/ml) and the methionine-Zinc (Zn) complex (2 mg/ml) (n=6). Mice were kept for 3 weeks after RRV infection. The course of rotavirus infection is described above.

TABLE 7

The results of efficacy test of drug candidates for rotavirus (RRV) infection

| Drug candidate | Sick | Not sick | Sick Rate(%) | Odds Ratio | 95% CI | P value |
|---|---|---|---|---|---|---|
| Saline | 6 | 1 | 86 | 30 | 1.47-612 | 0.03 |
| Metnionine-Zn | 1 | 6 | 14 | 0.03 | 0.001-0.55 | 0.03 |
| Neu5Ac + Meth-Zn* | 1 | 5 | 17 | 0.03 | 0.02-0.68 | 0.03 |

*Meth-Zn = Metnionine-Zn complex.

Pups pretreated with the drug candidates were not infected compared to control pups pretreated with saline. The results with statistical analysis are concluded in Table 7.

The effective dosages of drug candidates for rotavirus infection for human are calculated and listed in Table 8.

TABLE 8

The dosages of drug candidates for rotavirus infection

| Drug candidate | Low (mg/kg) | High (mg/kg) | Range (mg/kg) |
|---|---|---|---|
| Saline | 0.1 | 20 | 0.1-20 |
| Metnionine-Zn | 0.1 | 20 | 0.1-20 |
| Neu5Ac + Meth-Zn* | 0.1:0.1 | 20:20 | 0.1:0.1-20:20 |

*Meth-Zn = Metnionine-Zn complex.

8.2. An Animal Model of Later Term Embryo and Newborn Chicks

Four groups of day 16 (E16) chicken embryos were pretreated via allantois injection with 100 microliter of saline solution containing 1) saline alone (n=6); 2) 20 microliter of 2% diethyl disulfide (n=6); 3) 20 microgram of the *allium sativum* (n=6); and 4) 100 microgram of the Neu5Ac and 100 microgram of the methionine (n=6), followed by inoculation via allantois injection of 100 µl (microliter) of the 2009H1N1 influenza virus (California strain, titer: 1:128, diluted 100 times with saline) next day. Allantois fluid was collected at 48 hours after viral inoculation and viral titers in the fluid were determined by a direct hemagglutination test. The chicken embryos were kept culturing in a 35° C. incubator until the newborn chickens coming out.

Viral titers of 2009H1N1 California strain in allantois fluid (48 hours) are summarized below.

| Viral titers of 2009H1N1 (California) virus in allantois fluid (48 hours) | | | | | | |
|---|---|---|---|---|---|---|
| Chicken embryo | 1 | 2 | 3 | 4 | 5 | 6 |
| Saline | 4+ | 4+ | 4+ | 4+ | 4+ | − |
| Diethyl disulfide | 2+ | − | − | + | − | − |
| *Allium sativum* | − | − | − | − | − | − |
| Neu5Ac + Methionine | + | − | − | − | − | + |

The group-1 (virus control) newborn chicks looked sick and the newborn chicks of group-2 (diethyl disulfide), group-3 (garlic) and group-4 (formula) looked healthy. As summarized in Table 9, diethyl disulfide, *allium sativum* and the formula significantly inhibited infections of later term chicken embryos by the 2009 H1N1 and seasonal H1N1 viruses.

TABLE 9

The results of chicken embryo test of drugs against 2009H1N1 virus infection

| Drug candidate | Sick | Not sick | Sick Rate(%) | Odds Ratio | 95% CI | P value |
|---|---|---|---|---|---|---|
| Saline | 5 | 1 | 83 | ND* | ND | ND |
| Diethyl disulfide | 1 | 5 | 17 | 0.04 | 0.002-0.83 | 0.08 |
| *Allium sativum* | 1 | 6 | 14 | 0.03 | 0.002-0.68 | 0.03 |
| Neu5Ac + Methionine | 1 | 5 | 17 | 0.04 | 0.002-0.83 | 0.08 |

*ND = Not Difined.

The animal model of later term embryo (E16-E20) and newborn chicken can be used but not limited for the screening of anti-influenza virus drugs.

9. Antibodies for Prevention and Treatment of Influenza Infections

Following immune sera were tested for its efficacy on prevention and treatment of viral infections as described below.
- a. Chicken immune serum against the 2009H1N1 influenza virus (California strain) (National influenza Center of China CDC).
   Immunogen: purified 2009H1N1 influenza virus (California strain).
   Antibody titer: 1:1280 (10 times dilution to 1:128).
- b. Goat immune serum against a seasonal H1N1 influenza virus (Shanghai, 1999) (National influenza Center of China CDC).
   Immunogen: purified seasonal H1N1 influenza virus (Shanghai, 1999).
   Antibody titer: 1:128.
- c. Goat immune serum against a H3N2 influenza virus (Jiangxi, 2004) (National influenza Center of China CDC).
   Immunogen: the H3N2 influenza virus (Jiangxi, 2004).
   Antibody titer: 1:1280 (10 times dilution to 1:128).

d. Rabbit immune serum against a H5N1 influenza virus (Anhui, 2005) (National influenza Center of China CDC).

Immunogen: purified H5N1 influenza virus (Anhui, 2005).

Antibody titer: 1:1280 (10 times dilution to 1:128).

e. Human serum pool containing low level of antibodies to seasonal-H1N1 influenza virus (China 2009) (National influenza Center of China CDC).

Antibody titer for influenza H1N1, H3N2 and B viruses: 1:5.

All the immune sera except the anti-2009H1N1 (California) sera mentioned above did not react to the 2009H1N1 (California) influenza virus determined by a hemagglutination test.

9.1. A Newborn Mouse Model for the Treatment of Influenza Infection

Three groups of newborn bulb/c pups were inoculated at day 5 (P5) via nasal and oral administration of 30 µl (microliter) of the A/PR/8/34 (H1N1) influenza virus (titer: 1:512, diluted 300 times with saline); and were treated at day 6 (P6) via intraperitoneal injection with 100 µl of saline containing 1) saline alone (n=6); 2) 20 µl (microliter) of the chicken anti-2009H1N1 influenza virus serum (antibody titer: 1:128) (n=7); 3) 20 µl (microliter) of the chicken anti-2009H1N1 influenza virus serum pre-treated with 10 µl (microliter, 100 µg) of the NeuSAc (10 mg/ml) (total=20 µl, incubated for 30 minutes) (n=7); and 4) 20 µl (microliter) of the formula consisted of NeuSAc (200 µg) and 2% diethyl disulfide (n=6). Mice were kept for 7 days after treatment.

As summarized in Table 10, 5/6 (83%) of the pups treated with saline and all (100%) of the pups treated with the anti-2009H1N1 serum alone were died at day 2 after viral infection. Only 1/7 (14.3%) of the pups treated with the formula consisted of anti-2009H1N1 serum+NeuSAc, and 2/7 (28.6) of the pups treated with the formula consisted of NeuSAc+methionine were died at day 2 after viral infection. The results indicated that the formula consisted of anti-20009H1N1 antibodies and Neu5Ac reduced the death rate of the highly pathogenic A/PR/8/34(H1N1) infection from 83.3% to 14.3% (5.9 folds); and the formula consisted of Neu5Ac and methionine reduced the death rate of the A/PR/8/34 (H1N1) infection from 83.3% to 28.6% (2.8 folds). The data also suggested that high dose of the anti-20009H1N1 antibodies alone are harmful rather than helpful for the treatment of the A/PR/8/34 (H1N1) infection in newborn mouse pups.

TABLE 10

The results of bulb/c mouse test of drugs against the A/PR/8/34(H1N1) virus infection

| Drug candidate | Death | No death | Death Rate(%) | Odds Ratio | 95% CI | P value |
|---|---|---|---|---|---|---|
| Saline | 5 | 1 | 83.3 | ND* | ND | ND |
| H1N1-Ab.1[a] | 7 | 0 | 100 | ND | ND | ND |
| H1N1-Ab.1 + Neu5Ac | 1 | 6 | 14.3 | 0.03 | 0.002-0.68 | 0.03 |
| Neu5Ac + Methionine | 2 | 5 | 28.6 | 0.08 | 0.005-1.19 | 0.10 |

*ND = Not Difined.

9.2 A Newborn Mouse Model for the Prevention of Influenza Infection

Eight groups of newborn bulb/c mouse pups were pre-treated at day 6 (P6) via intraperitoneal injection with 50 µl of saline solution containing 1) saline alone (control group, n=6); 2) 10 µl (microliter) of the chicken anti-2009H1N1 serum (n=7); 3) 10 µl (microliter) of the goat anti-seasonal H1N1 serum (n=7); 4) 10 µl (microliter) of the human serum pool (n=5); 5) 10 µl (microliter) of the goat anti-H3N2 serum (n=5); 6) 10 µl (microliter) of the rabbit anti-H5N1 serum (n=6); 7) 10 µl (microliter) of the chicken anti-2009H1N1 influenza virus serum pre-treated with 10 µl (microliter, 300 µg) of the Neu5Ac (30 mg/ml) (incubated for 30 minutes) (n=5); and 8) 10 µl (microliter) of the chicken anti-2009H1N1 influenza virus serum plus 10 µl (microliter) of the human serum pool (n=5). The pups were inoculated at day 7 (P7) via oral administration of 50 µl (microliter) of the A/PR/8/34 (H1N1) virus (titer: 1:512, diluted 100 times with saline), and kept for 7 days after viral infection.

The results are summarized in Table 11. The data indicated that 1) the formula consisted of anti-2009H1N1 antibodies+Neu5Ac or antibodies against H5N1 are significantly effective for the prevention of the A/PR/8/34 (H1N1) influenza virus infection; 2) the human serum pool containing lower dose of anti-seasonal H1N1 antibodies (H1N1-Ab.3, 1:5) reduced the death rate of the A/PR/8/34 (H1N1) infection from 83.3% to 40.0% (2.1 folds); 3) the serum containing higher dose of anti-seasonal H1N1 antibodies (H1N1-Ab.2, 1:128) is not effective for the prevention of the A/PR/8/34 (H1N1) infection; and 4) the serum containing higher dose of anti-2009H1N1 antibodies (H1N1-Ab.1, 1:128) is not effective or harmful for the prevention of the A/PR/8/34 (H1N1) infection of newborn pups.

TABLE 11

The mouse test of antibodies for preventing the A/PR/8/34(H1N1) viral infection

| Treatment | n= | No death | Death (%) | Odds Ratio | 95% CI | P |
|---|---|---|---|---|---|---|
| Saline | 6 | 1 | 5 (83.3) | 1.4 | 0.07-28.1 | 1.0 |
| H1N1-Ab.1[a] | 7 | 0 | 7 (100) | Infinity | Infinity | Infinity |
| H1N1-Ab.2[b] | 7 | 0 | 7 (100) | Infinity | Infinity | Infinity |
| H1N1-Ab.3[c] | 5 | 3 | 2 (40.0) | 0.13 | .008-2.2 | 0.24 |
| H3N2-Ab | 5 | 0 | 5 (100) | Infinity | Infinity | Infinity |
| H5N1-Ab | 6 | 5 | 1 (16.7) | 0.04 | .002-0.83 | 0.08 |
| H1N1-Ab.1 + Neu5Ac | 6 | 5 | 1 (16.7) | 0.04 | .002-0.83 | 0.08 |
| H1N1-Ab.1 + Ab.3 | 5 | 2 | 3 (60.0) | 0.30 | 0.02-4.91 | 0.55 |

[a]Chicken anti-2009 H1N1 (California, 2009) serum, 1:128;
[b]Goat anti-seasonal H1N1 (Shanghai, 1999) serum, 1:128;
[c]Human serum pool: anti-H1N1 (China, 2009): 1:5.

The animal models described above can be used but not limited for rapid evaluation of the efficacy and side effect of vaccines and antibodies among other ages of animals or people.

9.3. A Newborn Chick Model for Influenza Infection

Five groups of day 16 (E16) chicken embryos were treated via allantois injection of each 100 µl (microliter) of 1) saline alone (n=6); 2) the chicken anti-2009H1N1 influenza virus serum (1:128, n=9); 3) the goat anti-seasonal H1N1 serum (1:128, n=8); 4) the human serum pool (1:5, n=6); 5) the chicken anti-2009H1N1 (California) serum (1:128) pre-treated with 10 µl (microliter, 300 µg) of the Neu5Ac (30 mg/ml) (incubated for 30 minutes) (n=8). Next day (E17), chicken embryos were inoculated via allantois injection of 100 μl (microliter) of the 2009H1N1 influenza virus (California strain, titer: 1:128, diluted 100 times with saline). The chicken embryos were kept culturing in a 35° C. incubator until the newborn chicks coming out.

The data indicated that the formula consisted of anti-2009H1N1 antibodies+Neu5Ac are significantly effective for the prevention of the 2009H1N1 influenza virus infection (Table 12, FIG. 12D); and the other sera containing moderate or high dose of anti-influenza virus antibodies (H1N1-Ab.1 and H1N1-Ab.2) are harmful rather than effective for the prevention of the 2009H1N1 virus infection (FIGS. 12B and 12C) although they have lower death rates (Table 12).

TABLE 12

The results of chicken test of antibodies for preventing 2009H1N1 influenza viral infection

| Treatment | n= | Not sick | Sick (%)* | Death (%) | Odds Ratio | 95% CI | P |
|---|---|---|---|---|---|---|---|
| Virus alone** | 6 | 1 | 5 (83.3) | 3 (50.0) | 0.83 | 0.04-17.0 | 1.0 |
| H1N1-Ab.1 + Virus | 9 | 1 | 8 (88.9) | 2 (22.2) | 1.2 | 0.06-24.5 | 1.0 |
| H1N1-Ab.2 + Virus | 8 | 1 | 7 (87.5) | 3 (37.5) | 1.4 | 0.07-28.1 | 1.0 |
| H1N1-Ab.3 + Virus | 6 | 1 | 5 (83.3) | 2 (33.3) | 1.0 | 0.05-20.8 | 1.0 |
| H1N1-Ab.1 + Neu5Ac | 8 | 7 | 1 (12.5) | 1 (12.5) | 0.03 | .001-0.57 | 0.03 |

*including death;
**2009H1N1 (California) influenza virus;
a: chicken anti-2009H1N1(California) serum, 1:128;
b: goat anti-seasonal H1N1(Shanghai, 1999) serum, 1:128;
c: human serum pool: anti-H1N1 (China, 2009): 1:5.

The animal model of later term embryo (E16-E20) and newborn chicks can be used but not limited for evaluation of the efficacy and safety of influenza vaccines and antibodies.

10. Experimental Models for Evaluation of Vaccines and Antibodies 10.1. An Animal Model for Rapid Evaluating the Safety of Vaccines and Antibodies Six groups of day 16 (E16) chicken embryos were treated via allantois injection of each 100 μl (microliter) of 1) saline alone (n=10); 2) the chicken anti-2009H1N1 influenza virus serum (n=11); 3) the goat anti-seasonal H1N1 serum (n=11); 4) the human serum pool (n=8); 5) the goat anti-H3N2 serum (n=10); 6) the rabbit anti-H5N1 serum (n=8); The chicken embryos were kept culturing in a 35° C. incubator until the newborn chicks coming out.

Figure 13:
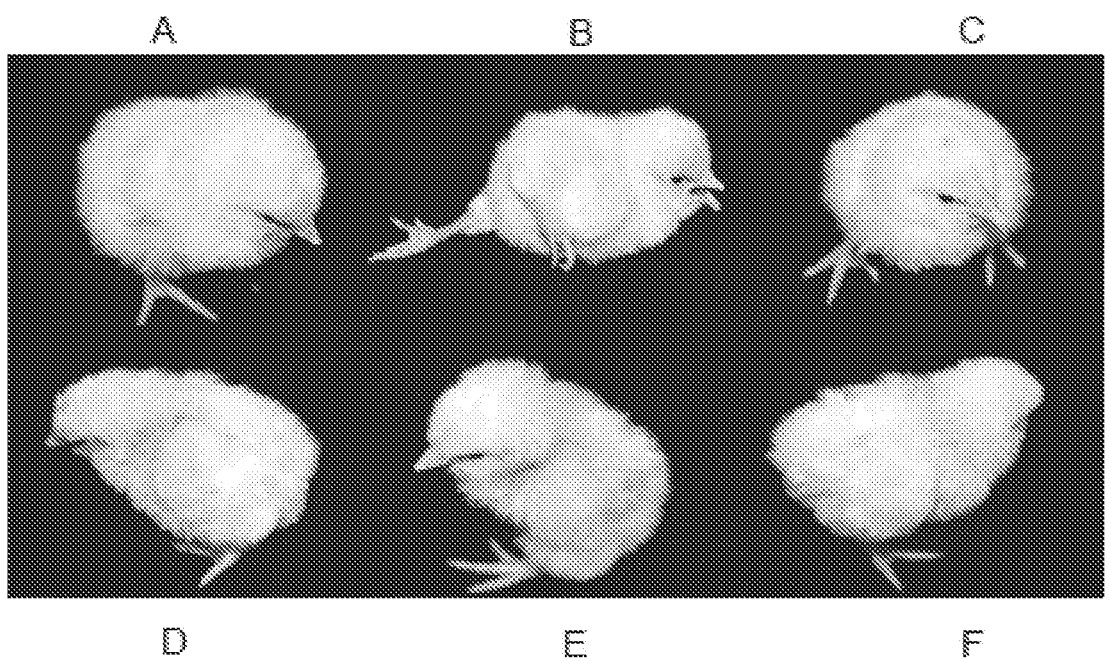
FIG. 13 is a graphical representation of newborn chicks treated at E16 with saline (A), anti-2009H1N1 (California) virus serum (B), anti-seasonal H1N1 (Shanghai, 1999) virus serum (C), anti-H3N2 (Jiangxi, 2004) virus serum (D), anti-H5N1 (Anhui, 2005) virus serum (E), and a healthy human serum pool (F).

The results are summarized in Table 13 and FIG. 13. The chicks treated with the anti-2009H1N1 serum (FIG. 13B), the anti-seasonal H1N1 serum (FIG. 13C), and the anti-H5N1 serum (FIG. 13E) looked sick. However, the chicks treated with saline (FIG. 13A), the anti-H3N2 serum (FIG. 13D), and the human serum pool (FIG. 13F) looked healthy. The data indicated that moderate or high dose of anti-H1N1 and anti-H5N1 antibodies induced either death or severe disease in chicken fetus and newborn chicks.

TABLE 13

The results of chicken test of the efficacy and safty of antibodies against influenza viruses

| Treatment | n= | Not sick | Sick (%)* | Death (%) | Odds Ratio | 95% CI | P |
|---|---|---|---|---|---|---|---|
| Saline | 10 | 9 | 1 (10) | 1 (10) | 1.1 | 0.06-20.5 | 1.0 |
| H1N1-Ab.1[a] | 11 | 1 | 10 (91) | 2 (18) | 90 | 4.9-1660 | 0.0003 |
| H1N1-Ab.2[b] | 11 | 2 | 9 (82) | 5 (46) | 41 | 3.09-530 | 0.002 |
| H1N1-Ab.3[c] | 8 | 7 | 1 (13) | 1 (13) | 1.29 | 0.07-24.3 | 1.00 |
| H3N2-Ab | 10 | 7 | 3 (30) | 3 (30) | 3.86 | 0.33-45.6 | 0.58 |
| H5N1-Ab | 8 | 4 | 4 (50) | 1 (13) | 9.0 | 0.81-100 | 0.14 |

*including death;
[a]chicken anti-2009H1N1(California) serum, 1:128;
[b]goat anti-seasonal H1N1(Shanghai, 1999) serum, 1:128;
[c]human serum pool: anti-H1N1 (China, 2009): 1:5.

10.2. An Animal Model of Guillain-Barre Syndrome

Injection of the anti-2009H1N1 serum, the anti-seasonal H1N1 serum and the anti-H5N1 serum into E16 chicken embryo as described above induced the leg disability of newborn chicks (FIGS. 13B, 13C, and 13D) which is similar to the Guillain-Barre syndrome (GBS) in human. The frequencies of GBS induced by the anti-influenza virus antibodies are listed in Table 14. The results indicated that the antibodies induced by the 2009H1N1 (California) virus is at highest risk for inducing GBS, followed by antibodies induced by the avian H5N1 (Anhui, 2005) virus and the seasonal-H1N1 (Shanghai, 1999) virus.

TABLE 14

The frequency of Guillain-Barre syndrome induced by anti-influenza antibodies

| Treatment | n= | Not sick | GBS (%)* | OR | 95% CI | P |
|---|---|---|---|---|---|---|
| Saline | 10 | 9 | 0 (0.0) | Infinity | Infinity | Infinity |
| H1N1-Ab.1[a] | 11 | 1 | 8 (89) | 72 | 3.84-1350 | 0.001 |
| H1N1-Ab.2[b] | 11 | 2 | 4 (67) | 18 | 1.24-261 | 0.04 |
| H1N1-Ab.3[c] | 8 | 7 | 0 (0.0) | Infinity | Infinity | Infinity |
| H3N2-Ab | 10 | 7 | 0 (0.0) | Infinity | Infinity | Infinity |
| H5N1-Ab | 8 | 4 | 4 (50) | 9.0 | 0.81-100 | 0.14 |
| H1N1-Ab.1 + Neu5Ac | 6 | 5 | 0 (0.0) | Infinity | Infinity | Infinity |

*Guillain-Barre syndrome;
[a]chicken anti-2009H1N1(California) serum, 1:128;
[b]goat anti-seasonal H1N1(Shanghai, 1999) serum, 1:128;
[c]human serum pool: anti-H1N1 (China, 2009): 1:5.

The animal model of later term embryo (E16-E20) and newborn chicks can be used but not limited for evaluation of the efficacy and safety of influenza vaccines and antibodies, for the pathogenesis study of GBS and for screening drugs for the prevention and treatment of GBS and side effect of vaccines and antibodies.

11. Therapeutic Application of Neu5Ac for Influenza Infection 11.1. Treatment of the Side Effect of Influenza Vaccines and Antibodies with Neu5Ac Each 100 μl (microliter) of the sera containing H1N1-Ab.1, -Ab.2 and the H5N1-Ab were incubated with each 10 μl (microliter, 300 μg) of the Neu5Ac (30 mg/ml) for 30 minutes, then were administrated via allantois injection into three groups of day 16 (E16) chicken embryos: 1) the chicken anti-2009H1N1 pre-treated serum (n=8); 2) the goat anti-seasonal H1N1 pre-treated serum (n=8); and 3) the rabbit anti-H5N1 pre-treated serum (n=8). The chicken embryos were kept culturing in a 35° C. incubator until the newborn chicks coming out.

The results are summarized in Table 11 and Table 12. The data show that the newborn chicks with injection of the immune sera pre-treated with N-acetylneuraminic acid (Neu5Ac) developed neither disorders nor GBS.

11.2. Further, the immune sera pre-treated with Neu5Ac are effective for prevention and treatment of influenza infections caused by the 2009H1N1 (California) virus in newborn chicks as described above (Table 10, FIG. 12D).

12. In Vivo Proof of a Novel Acting Mechanism of Vaccination and Antibody Therapy In vitro and in vivo proof of a novel mechanism of vaccination and passive immunity has been described in PCT/US2007/018258 and U.S. 61/278,685.

For further in vivo proof, the blood were collected from the newborn chicks treated with injection of anti-influenza immune sera as mentioned in 10.1 and 11.1 (Table 11); and the chicks were infected at P3 (day 8 after serum injection) via nasal drop and oral administration of 100 μl (microliter) of the 2009H1N1 (California) virus (1:32, 2 times dilution). The chicks were kept for 4 days after viral infection for observation of influenza symptoms.

TABLE 15

The results of chicken test of the efficacy of antibodies against the 2009 H1N1 influenza virus

| Treatment | n= | Not sick | Sick (%)* | Death (%) | Odds Ratio | 95% CI | P |
|---|---|---|---|---|---|---|---|
| Saline | 9 | 1 | 8 (89) | 1 (11) | 64 | 3.38-1210 | 0.003 |
| H1N1-Ab.1$^a$ | 9 | 6 | 3 (33) | 3 (33) | 0.06 | .005-0.76 | 0.05 |
| H1N1-Ab.2$^b$ | 6 | 5 | 1 (17) | 0 (0.0) | 0.03 | 0.001-0.50 | 0.01 |
| H1N1-Ab.3$^c$ | 7 | 2 | 5 (71) | 4 (57) | 0.31 | 0.02-4.41 | 0.55 |
| H3N2-Ab | 7 | 1 | 6 (86) | 4 (57) | 0.75 | 0.04-14.6 | 1.00 |
| H5N1-Ab | 7 | 4 | 3 (43) | 3 (43) | 0.09 | 0.007-1.22 | 0.11 |

*including death;
$^a$chicken anti-2009H1N1(California) serum, 1:128;
$^b$goat anti-seasonal H1N1(Shanghai, 1999) serum, 1:128;
$^c$human serum pool: anti-H1N1 (China, 2009): 1:5.

As summarized in Table 15, at day 3 after virus infection, the newborn chicks with injection of the sera containing 2009H1N1-Ab (6/9, 63%), seasonal H1N1-Ab (5/6, 83%) and the H5N1-Ab (4/7, 57%) eight days ago were not infected by the 2009H1N1 (swine) virus. However, the newborn chicks with injection of the 2009H1N1 immune serum (3/9, 33%), the H3N2 immune serum (4/7, 57%) or the H5N1 immune serum (3/7, 43%) were died at day 3 after virus infection suggesting that those antibodies could cause worse viral infection in chick infants.

13. Identification of Glycan-Related Biological Markers

Binding of WGA to human healthy and disease tissues was detected with a tissue array chip consisted of FDA normal human organs (Array IAD+bonus malignant samples (Immgenex, San Diego, USA). The results showed that majority of normal human organs except bone marrow, salivary gland and hypophysis do not or weakly express N-Acetyl-D-Glucosamine, while following cancer tissues strongly express N-Acetyl-D-Glucosamine: malignant melanoma, brain malignant oligodendroglioma, kidney clear cell carcinoma, skin basal cell carcinoma of head, throat carcinoma, Hodgkin's lymphoma of supraclavicular, colon intermediate grade interstitialoma, thyoid medullary carcinoma and skin squamous cell carcinoma of left chest wall.

14. Prevention and Treatment of Influenza Infection of A549 Cells

Following drug candidates were tested.

1) the NeuSAc at the concentration of 3 mg/ml;
2) the NeuSAc methyl ester (Neu5AcMe) at the concentration of 3 mg/ml;
3) the methionine at the concentration of 3 mg/ml;
4) formula-1 consisted of the NeuSAc (2 mg/ml) and Diethyl disulfide (2%);
5) formula-2 consisted of the Neu5AcMe (2 mg/ml) and the Diethyl disulfide (2%); 50 μl (microliter) of each drug candidate was added into monolayer of the human lung adenocarcinoma epithelial cells (A549 cell line) in a 12-well plate, incubated for one hour, discarded the supernatant; then the cells were challenged with 100 μl (microliter) of 2009 influenza A H1N1 virus (California strain, 1:128, 50 times dilution), the seasonal H1N1 virus (Brisbane/59/2007, 1:256, 100 times dilution) or H3N2 virus (Brisbane/10/2007, 1:128, 50 times dilution) for one hour, discarded the supernatant and added culture medium containing 100 μl of each drug candidate as mentioned above. Two wells with medium alone without addition of drugs were used as controls. The culture supernatant was collected at 24 and 48 hours and used for a hemagglutination inhibition test. The experiment was performed duplicate.

The positive result (inhibiting effect) of the hemagglutination inhibition test was observed as RBC pellet at the bottom of a well; negative result (no inhibition) was observed as no RBC or partial pellet at the bottom of a well. The results are summarized below.

a. Infection of A549 cells with 2009 H1N1 influenza A virus (California strain).

| Well | 1-2 | 3-4 | 5-6 | 7-8 | 9-10 | 11-12 | Hours |
|---|---|---|---|---|---|---|---|
| Treatment | Medium | Neu5Ac | Neu5AcMe | Met* | Frm-1** | Frm-2 | |
| Viral | 2+ | − | + | − | − | − | 24 |
| titer | 4+ | + | 2+ | + | − | + | 48 |

*Met = methionine; and
**Frm = formula as mentioned above.

b. Infection of A549 cells with seasonal H1N1 (Brisbane) influenza A virus.

| Well | 1-2 | 3-4 | 5-6 | 7-8 | 9-10 | 11-12 | Hours |
|---|---|---|---|---|---|---|---|
| Treatment | Medium | Neu5Ac | Neu5AcMe | Met* | Frm-1** | Frm-2 | |
| Viral | 4+ | − | − | − | − | + | 24 |
| titer | 4+ | + | + | 2+ | + | 2+ | 48 | c. Infection of A549 cells with influenza A virus H3N2 (Brisbane) strain.

| Well | 1-2 | 3-4 | 5-6 | 7-8 | 9-10 | 11-12 | Hours |
|---|---|---|---|---|---|---|---|
| Treatment | Medium | Neu5Ac | Neu5AcMe | Met* | Frm-1** | Frm-2 | |
| Viral | 3+ | + | + | − | + | + | 24 |
| titer | 4+ | 2+ | 2+ | + | 2+ | 3+ | 48 |

*Met = methionine; and
**Frm = formula as mentioned above.

The above results show that in the A549 cellular culture system, the drug candidates inhibited the infection of influenza virus 2009 H1N1, seasonal H1N1 and H3N2.

15. Prevention and Treatment of Influenza Infection of Mice 15.1. Antibodies from Pregnant Mother Induced Disease in Fetus or Newborns Human immune sera collected from subjects either with influenza infection or immunized with influenza vaccines were injected into pregnant bulb/c mouse dams via intraperitoneal injection at E19 (Table 8). The titers of those sera were adjusted to 1:128 and 200 microliter of each serum was used. Human serum pool consisted sera from 5 healthy individuals and the serum from a RSV infected subject were used as controls. The titer of the human serum pool to seasonal influenza H1N1, H3N2 and B viruses was 1:5. The death rates of the fetus or newborns delivered to those dams are summarized in Table 16.

TABLE 16

The death rates of fetus or newborns

| Immune Serum<br>One injection at E19 | N= | Deaths | Death<br>Rate(%) | Odds<br>Ratio | 95% CI | P<br>value |
|---|---|---|---|---|---|---|
| Hum* serum pre-vaccinization | 12 | 0 | 0.00 | Infinity | Infinity | Infinity |
| Human anti-RSV (infection) | 15 | 1 | 6.70 | 0.93 | 0.05-16.4 | 1.00 |
| Hum anti-09H1N1 post-vaccine | 12 | 6 | 50.0 | 14.0 | 1.37-143 | 0.02 |
| Hum anti-S-H1N1** post-vaccine | 14 | 3 | 21.4 | 3.82 | 0.35-42.0 | 0.33 |
| Hum anti-H5N1 post-infection | 18 | 9 | 50.0 | 14.0 | 1.51-130 | 0.009 |
| Rabbit anti-H5N1 | 12 | 6 | 50.0 | 14.0 | 1.37-143 | 0.02 |

*Hum = human;
**S = seasonal.

The results and the animal model provide direct evidence that a high level of anti-2009H1N1 and anti-H5N1 antibodies can cause severe side effect even death in fetuses and newborns. Furthermore, this finding suggests that vaccinating pregnant mothers with the 2009H1N1 (swine) influenza vaccine or a H5N1 vaccine is risky for the fetuses and newborns.

15.2. Treatment of Influenza Infection of Newborn Mice

Four groups of newborn bulb/c pups were inoculated at day 5 (P5) via nasal and oral administration of 20 μl (microliter) of the A/PR/8/34 (H1N1) influenza virus strain (titer: 1:256, diluted 200 times with saline); and were treated at day 2, 3, 4 and 5 via intraperitoneal injection with 100 μl of saline containing 1) saline alone (n=10); 2) 150 microgram of NeuSAcMe; 3) 30 μl of 2% diethyl disulfide plus 200 μg of the NeuSAcMe (n=10); and 4) 30 μl of 2% diethyl disulfide plus 200 μg of the NeuSAc (n=10). Mice were kept for 10 days after treatment.

9/10 (90%) of mice treated with saline alone died at day 3 or day 4 while 8/10 (80%) of the pups treated with diethyl disulfide+NeuSAcMe and 5/10 (50%) of the pups treated with either NeuSAcMe or diethyl disulfide+NeuSAc survived. The data indicated that the formulas consisted of diethyl disulfide+NeuSAcMe (OR=0.03, 95% CI=0.002-0.37, p=0.005) are significantly effective for the treatment of a severe A/PR/8/34 (H1N1) influenza infection.

Other embodiments besides the above may be articulated as well. The terms and expressions therefore serve only to describe the disclosure by example only and not to limit the disclosure. It is expected that others will perceive differences, which while differing from the foregoing, do not depart from the spirit and scope of the disclosure herein described and claimed. All patents, patent publications, and other references cited herein are incorporated herein by reference in their entirety.

The invention claimed is:

1. A method of treating or preventing viral diarrhea, or an infectious disease caused by an influenza virus, a Newcastle disease virus, or a rotavirus in a patient, the method comprising administering to the patient a pharmaceutical composition comprising:

N-acetylneuraminic acid; and a compound of the structure:

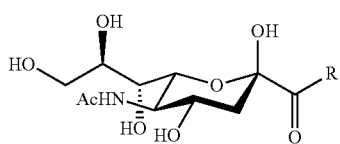

wherein
- R is hydrogen, alkoxy, alkyl, cycloalkyl, substituted alkyl, substituted cycloalkyl, aryl, substituted aryl, ether, thioester, disulfide ester, disulfide methyl, methionine, or phenol.

2. The method of claim 1, wherein the pharmaceutical composition is in the form of a tablet, a timed release tablet, a sustained release table, a capsule, a timed release capsule, or a sustained release capsule, a pill, a powder, granules, an elixir, a tincture, a solution, a suspension, a syrup, an emulsion, a nasal drop, an injectable, or an infusion, or conjugated to a nano-particle.

3. The method of claim 1, wherein the pharmaceutical composition is administered orally, subcutaneously, topically, intramuscularly, intravenously, intraperitoneally, intracavitally, transdermally, or via inhalation.

4. The method of claim 2, wherein the pharmaceutical composition further comprises a pharmaceutically acceptable carrier.

5. The method of claim 4, wherein the pharmaceutical composition is in the form of a powder or a granule.

6. The method of claim 4, wherein the pharmaceutical composition is in the form of a tablet, a capsule, or a pill.

7. The method of claim 6, wherein the tablet is a timed release tablet or a sustained release table.

8. The method of claim 6, wherein the capsule is a timed release capsule or a sustained release capsule.

9. The method of claim 4, wherein the pharmaceutical composition is in the form of an elixir, a tincture, a solution, a suspension, a syrup, or an emulsion.

10. The method of claim 4, wherein the pharmaceutical composition is in the form of a nasal drop.

11. The method of claim 4, wherein the pharmaceutical composition is in the form of an injectable or an infusion, or conjugated to a nano-particle.

* * * * *